(12) United States Patent
Berry

(10) Patent No.: US 9,724,087 B2
(45) Date of Patent: Aug. 8, 2017

(54) REPLACEABLE SUTURING HEAD, A REPLACEABLE NEEDLE CARTRIDGE, AND A SUTURING DEVICE

(71) Applicant: Sutrue Limited, Merseyside (GB)

(72) Inventor: Alexander Charles Berry, Merseyside (GB)

(73) Assignee: Sutrue Limited, Merseyside (GB)

( * ) Notice: Subject to any disclaimer, the term of this patent is extended or adjusted under 35 U.S.C. 154(b) by 155 days.

(21) Appl. No.: 14/399,601

(22) PCT Filed: May 8, 2013

(86) PCT No.: PCT/GB2013/051185
§ 371 (c)(1),
(2) Date: Nov. 7, 2014

(87) PCT Pub. No.: WO2013/167885
PCT Pub. Date: Nov. 14, 2013

(65) Prior Publication Data
US 2015/0127024 A1    May 7, 2015

(30) Foreign Application Priority Data

May 8, 2012  (GB) .................................. 1208024.8

(51) Int. Cl.
*A61B 17/04* (2006.01)
*A61B 17/06* (2006.01)
*A61B 17/00* (2006.01)

(52) U.S. Cl.
CPC ...... *A61B 17/0469* (2013.01); *A61B 17/0491* (2013.01); *A61B 17/06066* (2013.01); *A61B 2017/00398* (2013.01); *A61B 2017/00473* (2013.01); *A61B 2017/00734* (2013.01)

(58) Field of Classification Search
CPC ... A61B 17/04; A61B 17/0469; A61B 17/047; A61B 17/0472; A61B 17/0482; A61B 17/0483; A61B 17/0491; A61B 17/06066
See application file for complete search history.

(56) References Cited

U.S. PATENT DOCUMENTS

| 4,557,265 | A | | 12/1985 | Andersson |
| 4,899,746 | A | | 2/1990 | Brunk |
| 5,766,186 | A | | 6/1998 | Faraz et al. |
| 5,829,589 | A | * | 11/1998 | Nguyen ................ A61M 5/002 206/366 |

(Continued)

FOREIGN PATENT DOCUMENTS

| CA | 2008759 | 7/1991 |
| GB | 190818602 | 0/1908 |

(Continued)

*Primary Examiner* — Tuan V Nguyen
(74) *Attorney, Agent, or Firm* — Fogg & Powers LLC

(57) ABSTRACT

A replaceable suturing head for a suturing device includes a suturing portion. The suturing portion comprises a curved suturing needle arranged to move around a circular path defined by a plurality of rollers mounted on roller shafts within the suturing portion, at least one of the plurality of rollers being a drive roller driven by the drive motor to move the suturing needle around the circular path. One or more of the roller shafts is mounted within the suturing portion so that it can pivot around its base.

18 Claims, 35 Drawing Sheets

(56) References Cited

U.S. PATENT DOCUMENTS

| | | | |
|---|---|---|---|
| 5,835,828 A * | 11/1998 | Jyoroku | B01F 7/00175 222/DIG. 1 |
| 2002/0193809 A1 | 12/2002 | Meade et al. | |
| 2003/0083674 A1* | 5/2003 | Gibbens, III | A61B 17/0482 606/144 |
| 2005/0090709 A1 | 4/2005 | Okada et al. | |
| 2006/0224184 A1 | 10/2006 | Stefanchik et al. | |
| 2007/0239177 A1 | 10/2007 | Stokes et al. | |
| 2008/0249544 A1 | 10/2008 | Brand | |
| 2009/0024145 A1 | 1/2009 | Meade et al. | |
| 2009/0209980 A1 | 8/2009 | Harris | |
| 2010/0042116 A1* | 2/2010 | Chui | A61B 17/0482 606/145 |
| 2011/0054499 A1 | 3/2011 | Almodovar | |
| 2012/0265006 A1* | 10/2012 | Makower | A61B 17/0401 600/38 |

FOREIGN PATENT DOCUMENTS

| | | |
|---|---|---|
| GB | 2389313 | 12/2003 |
| RU | 2119771 | 10/1998 |
| WO | 9747246 | 12/1997 |
| WO | 2008147555 | 12/2008 |

\* cited by examiner

42

42

REPLACEABLE SUTURING HEAD, A REPLACEABLE NEEDLE CARTRIDGE, AND A SUTURING DEVICE

FIELD OF THE INVENTION

The present invention concerns a replaceable suturing head, a replaceable needle cartridge, and a suturing device.

BACKGROUND OF THE INVENTION

The suturing of the tissue of a human or animal body is traditionally done by hand using a curved suturing needle, which is often held using forceps. However, devices to aid suturing are known.

US 2009/024124 A (Meade et al.) discloses a suturing device with a drive mechanism that drives a curved suturing needle around a circular track. The curved suturing needle has an engagement surface, which is a notch into which the pawl of a drive arm engages to push the suturing needle around the circular track. The device is particularly intended to provide sufficient torque to drive the suturing needle through bony tissue.

US 2007/239177 A (Stokes et al.) similarly discloses a suturing device that drives a curved suturing needle around a circular track. The curved suturing needle may be driven by a smooth friction camming member, which as an arc-shaped member that contacts a portion of the suturing needle, and is moved around the circular track thus driving the suturing needle around the path by friction. Alternatively, the curved suturing needle may be driven by a toothed friction camming member, in which case the suturing needle is also toothed.

CA 2008759 A (Brunk Industries Inc.) discloses a suturing device that drives a curved suturing needle by means of four drive rollers that contact the diametrically outside surface of the suturing needle. The drive rollers are spaced so that at all time at least two are in contact with the suturing needle.

GB 2389313 A (Advanced Plastic technologies Limited) discloses a suturing device that drives a curved suturing needle by means of three drive rollers that contact the diametrically inside surface of the suturing needle.

There are various problems associated with these known suturing devices. The drive means used to rotate the suturing needles are often bulky, making the devices difficult to use. The drive means may require that special suturing needles are used, for example toothed suturing needles or suturing needles with notches. Alternatively, special suturing needles which cover a large part of a circle may be required so that the suturing needle is at all times in contact with sufficient components of the drive means to allow the suturing needle to be rotated successfully. Especially when in actual use, the suturing needles may be diverted from their intended circular path, which can affect the quality of the suturing, and in some cases can prevent the device from working altogether or even lead to the breakage of the suturing needle.

The present invention seeks to solve or mitigate some or all of the above-mentioned problems. Alternatively and/or additionally, the present invention seeks to provide an improved suturing device that can be used with existing standard-sized suturing needles.

SUMMARY OF THE INVENTION

In accordance with a first aspect of the invention there is provided a replaceable suturing head for a suturing device comprising a control assembly, the suturing head comprising a suturing portion;

wherein the suturing portion comprises a curved suturing needle arranged to move around a circular path defined by a plurality of rollers mounted on roller shafts within the suturing portion, at least one of the plurality of rollers being a drive roller driven by the drive motor to move the suturing needle around the circular path;

and wherein one or more of the roller shafts is mounted within the suturing portion so that it can pivot around its base.

By allowing the roller shafts to pivot around one end, i.e. their base, this allows the needle to move a certain distance in the direction of the axis of the shaft, as may be required for example if the needle is to pass through hard tissue such as bone without breaking. Advantageously, the base of the one or more roller shafts has a spherically-shaped end. This allows the roller shaft to be mounted in a spherical receiving hole in the suturing portion, which fixes the roller shaft in place while also allowing it to pivot.

Preferably, the suturing portion comprises biasing means for biasing the one or more roller shafts so that its roller is biased towards the suturing needle. This provides improved grip between the rollers and the suturing needle. It also keeps the shafts in position within the suturing portion, and allows the rollers to force the needle back into the central position. Advantageously, the biasing means is a spring plate mounted in parallel with the circular path of the suturing needle. The spring plate, acting in conjunction with rotating cogs and rollers and roller shafts, transmits mechanical tension onto the needle to allow for mechanical grip during rotation of the needle. The spring plate may be made of a sheet of resilient material, such as steel or nylon. Advantageously, the spring plate comprises a plurality of voids, and the roller shafts extend through the holes formed by the voids. This allows the spring plate to be positioned where it is in contact with the needle. Advantageously, the voids in the spring plate form shaft springs in the spring plate that press against the roller shafts. When the shafts have spherically-shaped ends, this advantageously allows them to pass easily through the voids of the spring plate during construction of the suturing head. Alternatively, the biasing means may be compression springs, leaf springs or any other biasing means that act to provide an appropriate bias to the shafts.

Advantageously, the suturing portion of the replaceable suturing head comprises a body portion, and a replaceable needle cartridge containing the suturing needle. This allows the needle cartridge to be replaced after a single use, while allowing the rest of the suturing head to be re-used. This is advantageous, as the suturing head will contains various mechanical components such as cogs and other elements and so is expensive to replace. However, as the suturing head is itself replaceable it can be replaced after a number of uses, for example when the cogs and other elements have become worn due to friction, without requiring the control assembly to be replaced at the same time. Preferably, the plurality of rollers are mounted on the body portion, and the replaceable needle cartridge comprises indentations into which the rollers extend to allow the rollers to contact the suturing needle. This allows the more expensive elements of the suturing head to be mounted in the body portion, so they do not need to be disposed of along with the needle cartridge. Preferably, the cartridge is configured and dimensioned for use with a standard size curved suturing needle. Advantageously, the replaceable needle cartridges are supplied directly from the suture manufacture significantly cutting down on packaging and risk of injury as current suture needles after use have to be disposed of with the potentially contaminated sharp end exposed.

Advantageously, the roller surfaces are arranged so they automatically drive the needle towards the centre of each roller. In combination with the cartridge the suture always remains central in the track of the head. In combination with the cartridge and plurality of rollers this acts to keep the suturing needle in place in the circular path. The roller or rollers comprise a curvilinear design which acting in plurality grip the suture needle. This allows force to be efficiently transmitted from the roller or rollers to the suturing needle, increasing the torque available. Advantageously, the roller design is curvilinear around its rotational surface and also along the surface perpendicular to the rotational surface. Advantageously, the rotational surface of at least one of the plurality of rollers is arranged to provide an indented drive surface. Advantageously, at least one of the plurality of rollers comprises a plurality of slotted recesses extending inwardly from its rotational surface. Preferably, of course, all rollers are arranged in this way. The slotted recesses allow the drive service to move flexibly. The surfaces of the roller in combination with a dimensional tolerance between the roller and the shaft allow the roller to sufficiently deviate from the diameter of the shaft to grip the suturing needle. Alternatively, the rollers may have a V-shaped groove. The groove may comprise teeth. The rollers may be made of a rubber material. Alternatively, the rollers may be made of a porous material, and have a coating of a rubber material.

Advantageously, the plurality of rollers comprise a first driven roller arranged on a first side of the circular track, and corresponding second and third free turning rollers arranged on the opposite side of the circular track from the first driven roller, and wherein the first, second and third rollers act to hold the suturing needle in the circular path. The three rollers will provide a triangular configuration that acts to hold the needle in position even when it is only in contact with those three rollers. The current pitch and roll of the suture is maintained via the cartridge which has a channel allowing the suture to maintain its path. Such a plurality of rollers may be provided at one or both extremes of the portion of the circular track covered by the body portion.

Advantageously, the cartridge portion comprises a cone-shaped indentation located on the circular track to guide the incoming end of the suturing needle into alignment with the circular path. Such a cone-shaped indentation may be provided at one or both extremes of portion of the circular track covered by the body portion.

Advantageously, the suturing head comprises a light to illuminate the suturing needle when it exits the body portion. The source of the light may be contained with the handle portion of the device. The light source may be provided by means of a fibre optic cable from the light source. The suturing head may comprise a dimple located adjacent to the circular track to indicate the point at which the suturing needle exits the body portion.

Preferably, the body portion of the suturing portion is open on a first side of the circular path. This allows the end suture thread attached to the needle to move around the circular path without becoming joined to the body portion. Further, this allows the cartridge to be removed from the body portion and the suturing needle can then be removed from the cartridge to allow suturing by hand, if required.

The suturing head may comprise a stem for attaching to the control assembly. The stem of the suturing head may be arranged to be attached to an endoscopic tube. Alternatively the stem of the suturing head may be arranged to be attached to a handle comprising the control assembly, which can be held while suturing.

In accordance with a second aspect of the invention there is provided a replaceable needle cartridge for a replaceable suturing head as described above. Advantageously, the replaceable needle cartridge contains a standard-size curved suturing needle.

In accordance with a third aspect of the invention there is provided a suturing device, comprising a control assembly comprising a drive motor and a control apparatus for controlling the drive motor; and a replaceable suturing head as described above.

Advantageously, the control assembly is arranged, in response to an input from a user, to position the suturing needle fully within the cartridge which is within the body portion of the suturing portion for removal of the disposable cartridge and or the replaceable suturing head. This allows the cartridge or suturing head to be safely removed and disposed of without risking injury from the suturing needle.

Advantageously, the control assembly is arranged, in response to an input from a user, to rotate the suturing needle once around the circular path. This assists in the suturing process.

In accordance with another aspect of the invention there is provided a replaceable suturing head for a suturing device comprising a control assembly, the suturing head comprising a stem for attaching to the control assembly, and a suturing portion mounted on the stem;

wherein the suturing portion comprises a curved suturing needle arranged to move around a circular path defined by a plurality of rollers mounted on roller shafts within the suturing portion, at least one of the plurality of rollers being a drive roller driven by the drive motor to move the suturing needle around the circular path;

and wherein the suturing portion of the replaceable suturing head comprises a body portion mounted on the stem, and a replaceable needle cartridge containing the suturing needle.

Advantageously, the plurality of rollers are mounted on the body portion, and the replaceable needle cartridge comprises indentations into which the rollers extend to allow the rollers to contact the suturing needle.

Other aspects of the invention are described in the following clauses:

1. A suturing device, comprising:
   a control assembly comprising a drive motor and a control apparatus for controlling the drive motor;
   a replaceable suturing head comprising a stem for attaching to the control assembly, and a suturing portion mounted on the stem;
   wherein the suturing portion comprises a curved suturing needle arranged to move around a circular path defined by a plurality of rollers mounted on shafts within the suturing portion;
   and wherein at least one of the plurality of rollers is a drive roller driven by the drive motor to move the suturing needle around the circular path.

2. A suturing device as described in clause 1, wherein the suturing portion of the replaceable suturing head comprises a body portion mounted on the stem, and a replaceable needle cartridge containing the suturing needle.

3. A suturing device as described in clause 2, wherein the plurality of rollers are mounted on the body portion, and the replaceable needle cartridge comprises indentations into which the rollers extend to allow the rollers to contact the suturing needle.

4. A suturing device as described in any preceding clause, wherein the roller shafts are mounted within the suturing portion so that they can pivot around one end.

5. A suturing portion as described in clause 4, wherein the suturing portion comprises biasing means for keeping the shafts in position within the suturing portion.

6. A suturing device as described in clause 5, wherein the biasing means is a spring plate mounted in parallel with the circular path of the suturing needle.

7. A suturing device as described in clause 6, wherein the spring plate comprises a plurality of cuts, and wherein the roller shafts extend through the holes formed by the cuts.

8. A suturing device as described in clause 7, wherein the cuts in the spring plate form shaft springs that hold the roller shafts in position within the suturing portion.

9. A suturing portion as described in any preceding clause, wherein the base of at least one the roller shaft has a spherically-shaped end.

10. A suturing device as claimed in any preceding clause, wherein the rotational surface of at least one of the plurality of rollers is arranged to provide an indented drive surface.

11. A suturing device as described in any preceding clause, wherein at least one of the plurality of rollers comprises a plurality of slotted recesses extending inwardly from its rotational surface.

12. A suturing device as described in any preceding clause, wherein the plurality of rollers comprise a first roller arranged on a first side of the circular track, and corresponding second roller and third rollers arranged on the opposite side of the circular track from the first drive roller, and wherein the first, second and third rollers act to hold the suturing needle in the circular path.

13. A suturing device as described in any preceding clause, wherein the body portion of the suturing portion comprises a cone-shaped indentation located on the circular track to guide an incoming the end of the suturing needle into alignment with the circular path.

14. A suturing device as described in any preceding clause, wherein the suturing head comprises a light to illuminate the suturing needle when it exits the body portion.

15. A suturing device as described in any preceding clause, wherein the body portion of the suturing portion is open on a first side of the circular path.

16. A suturing device as described in any preceding clause, wherein the control assembly is arranged, in response to an input from a user, to position the suturing needle fully within the body portion of the suturing portion for removal of the replaceable cartridge within the replaceable suturing head.

17. A suturing device as described in any preceding clause, wherein the control assembly is arranged, in response to an input from a user, to rotate the suturing needle once around the circular path.

18. A suturing device as described in any preceding clause, wherein the suturing head is configured and dimensioned for use with a standard-size curved suturing needle.

19. A suturing device as described in any preceding clause, wherein the body portion of the suturing portion contains a spring plate that, acting in conjunction with rotating gear and roller shafts, transmits mechanical tension onto the needle in both the tapered and non-tapered section to allow for mechanical grip during rotation of the needle.

20. A replaceable suturing head for a suturing device as described in any of clauses 1 to 17.

21. A replaceable cartridge for a suturing device as described in clause 2 or 3.

22. A replaceable suturing head as described in clause 20, or a replaceable cartridge as described in clause 21, containing a standard-size curved suturing needle.

It will of course be appreciated that features described in relation to one aspect of the present invention may be incorporated into other aspects of the present invention.

DESCRIPTION OF THE DRAWINGS

Embodiments of the present invention will now be described by way of example only with reference to the accompanying schematic drawings of which.

DETAILED DESCRIPTION

A suturing device in accordance with a first embodiment of the invention is now described with reference to FIGS. 1 to 33.

Figure 1:
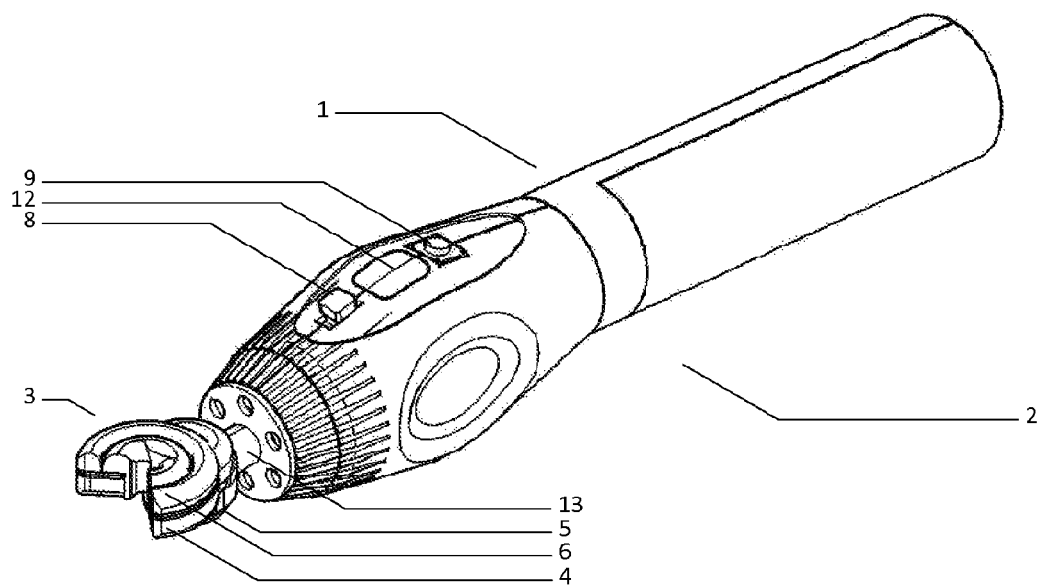
FIG. 1 shows an isometric view of a suturing device according to a first embodiment of the invention.
Figure 2:
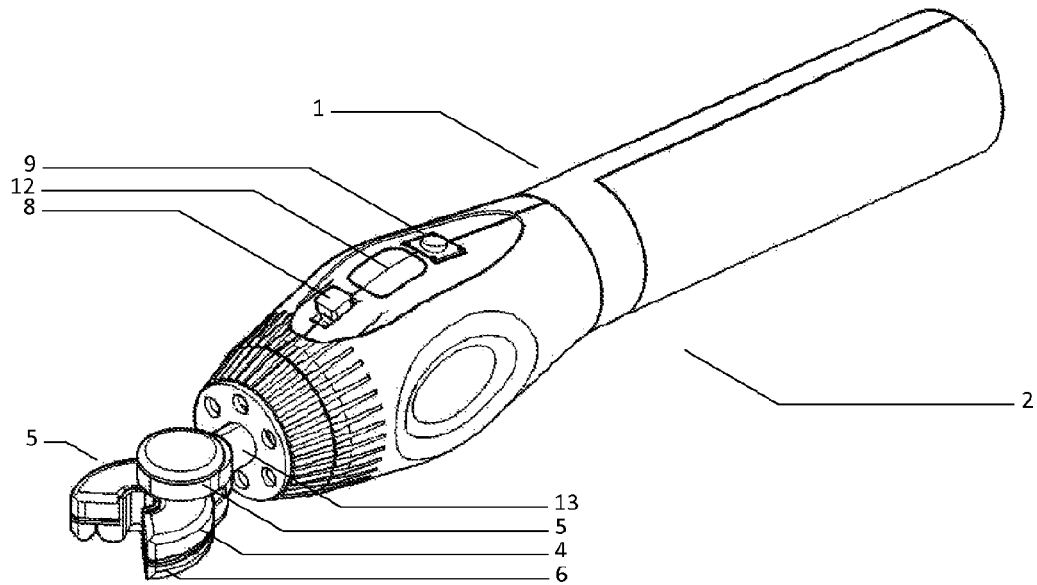
FIG. 2 shows an isometric view of the suturing device of FIG. 1 with the suturing head rotated.
Figure 3:
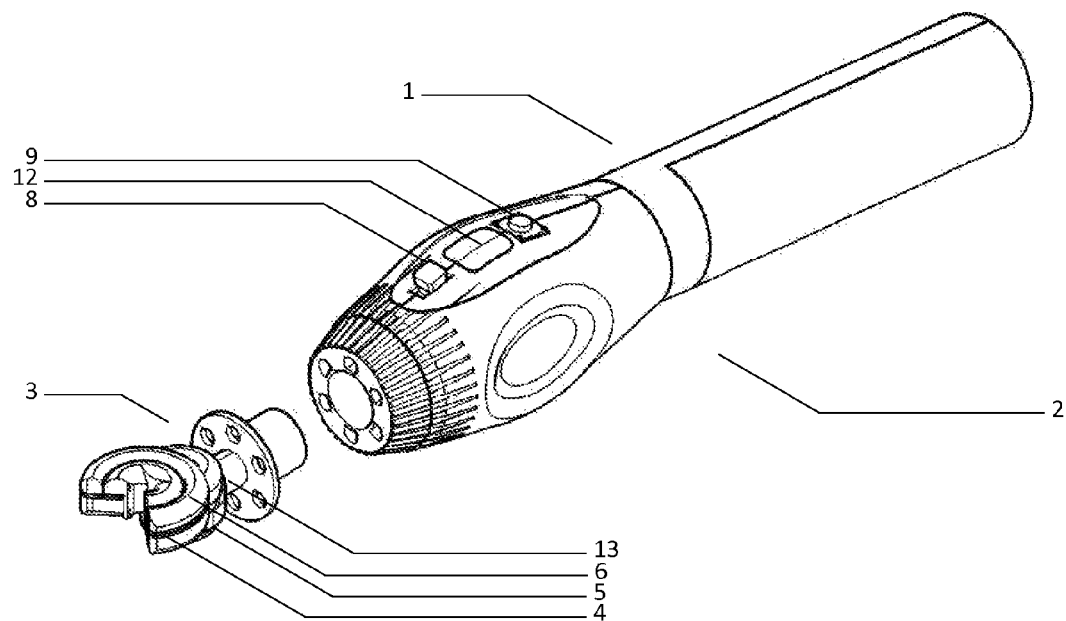
FIG. 3 shows an isometric view of the suturing device of FIG. 1 in two pieces.
Figure 4:
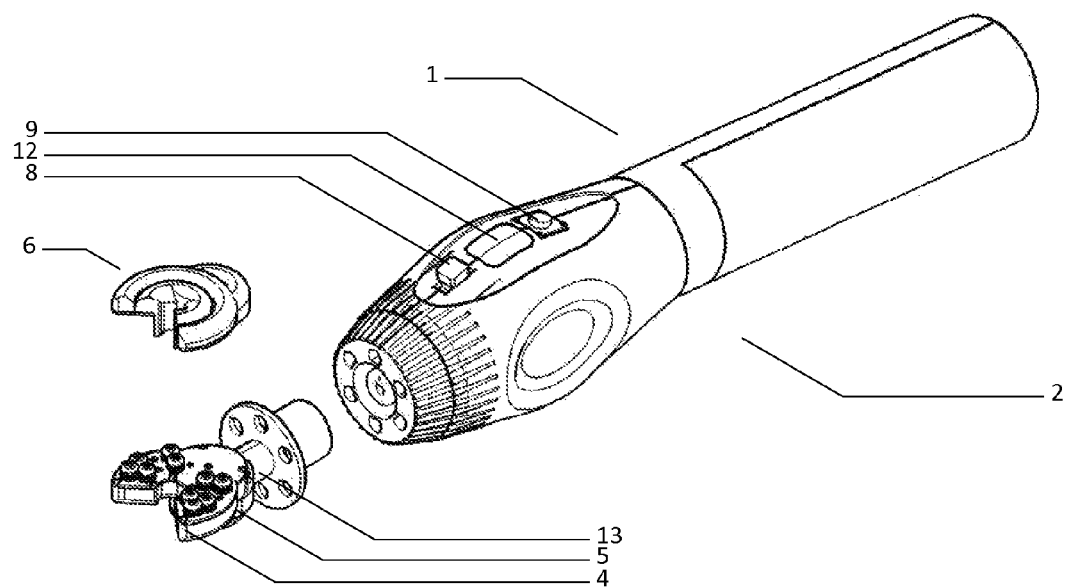
FIG. 4 shows an isometric view of the suturing device of FIG. 1 in three pieces.
Figure 5:
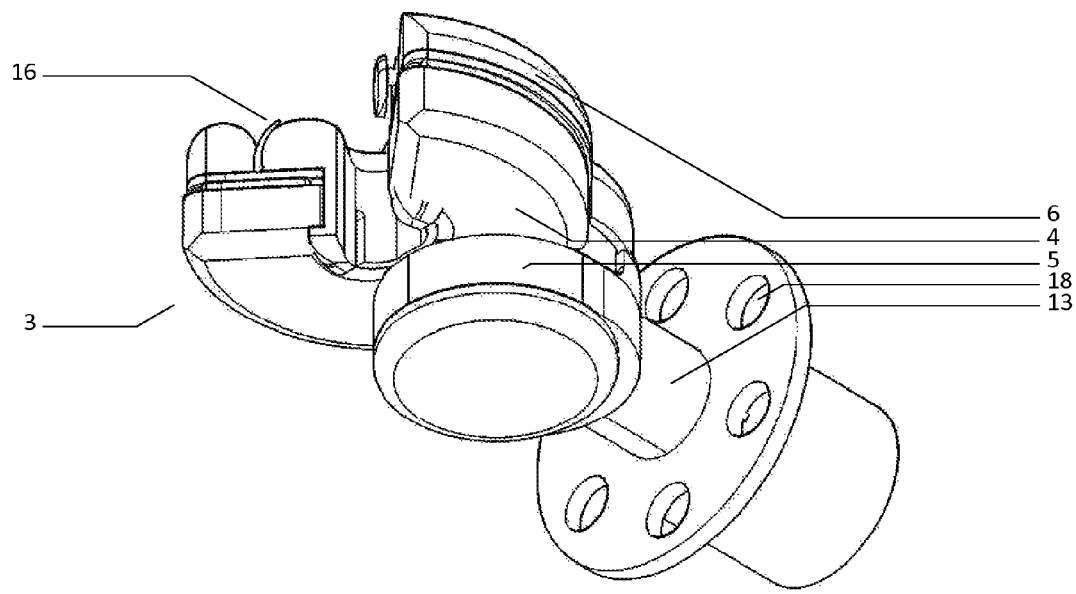
FIG. 5 shows an isometric view of the underside of the suturing head of the suturing device of FIG. 1.
Figure 6:
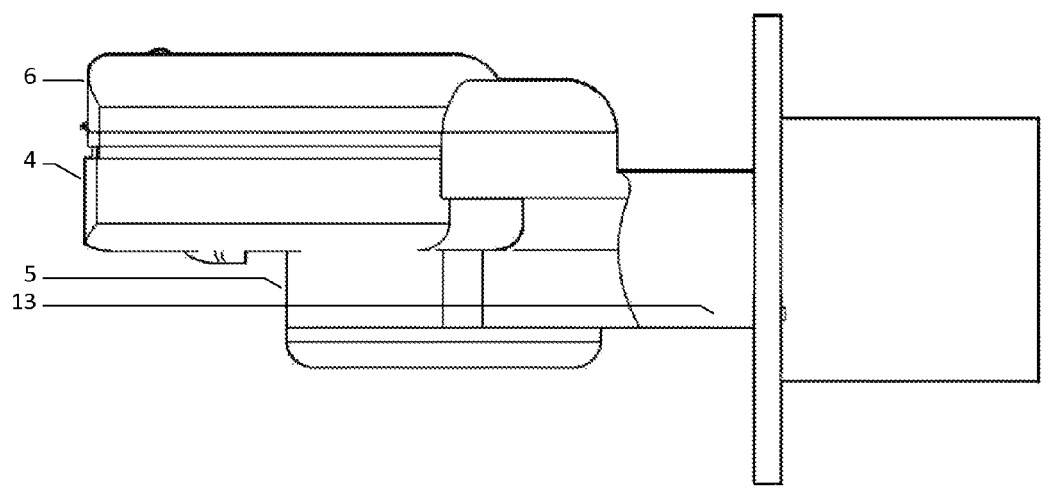
FIG. 6 shows a side view of the suturing head of the suturing device of FIG. 1.
Figure 7:
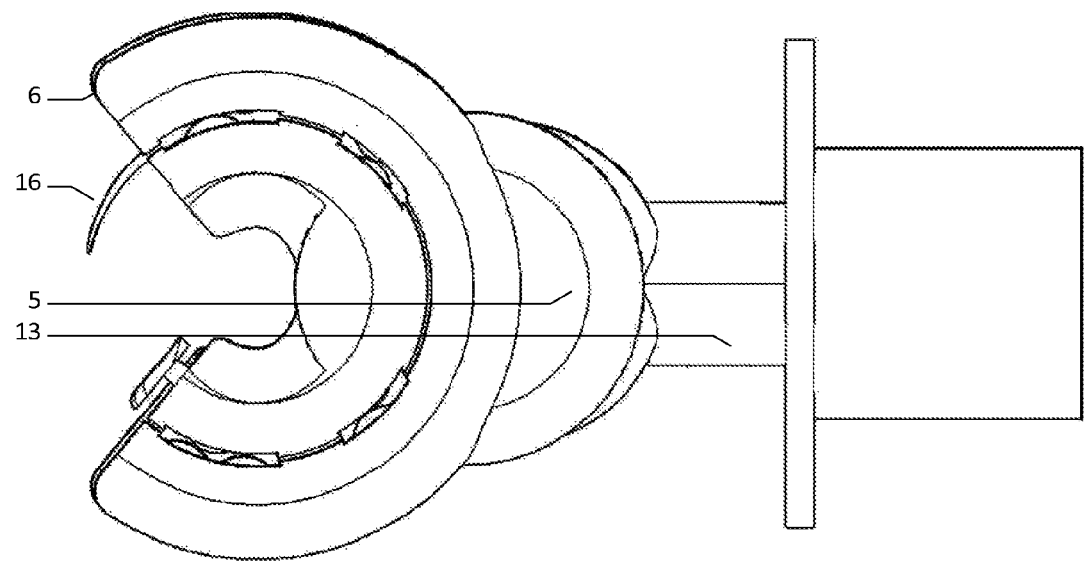
FIG. 7 shows a top view of the suturing head of the suturing device of FIG. 1 with the head in the fixed central position.
Figure 8:
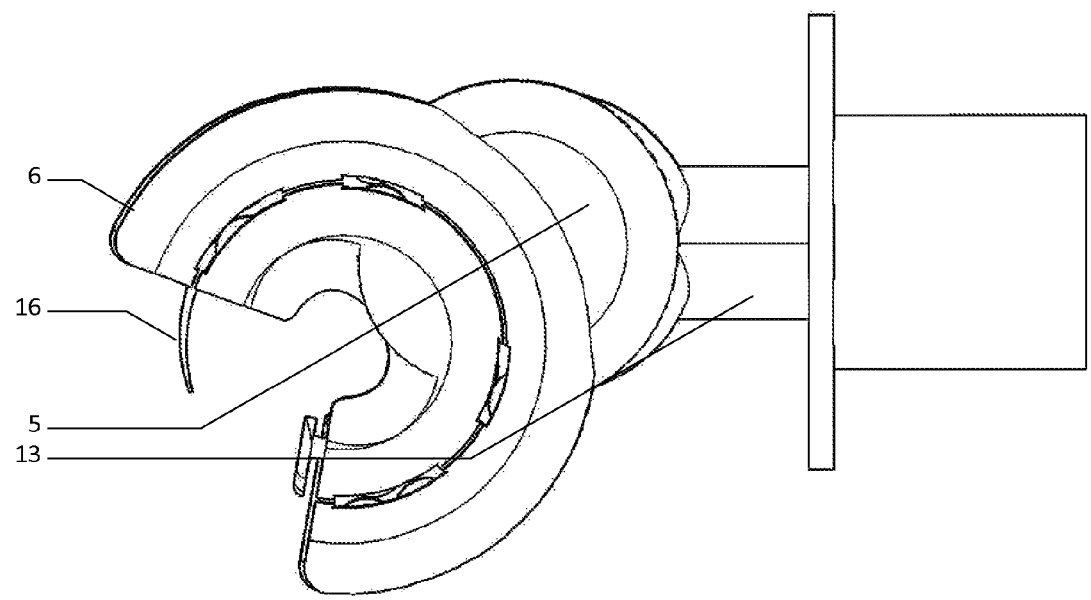
FIG. 8 shows a top view of the suturing head of the suturing device of FIG. 1 with the head in a rotated position.
Figure 9:
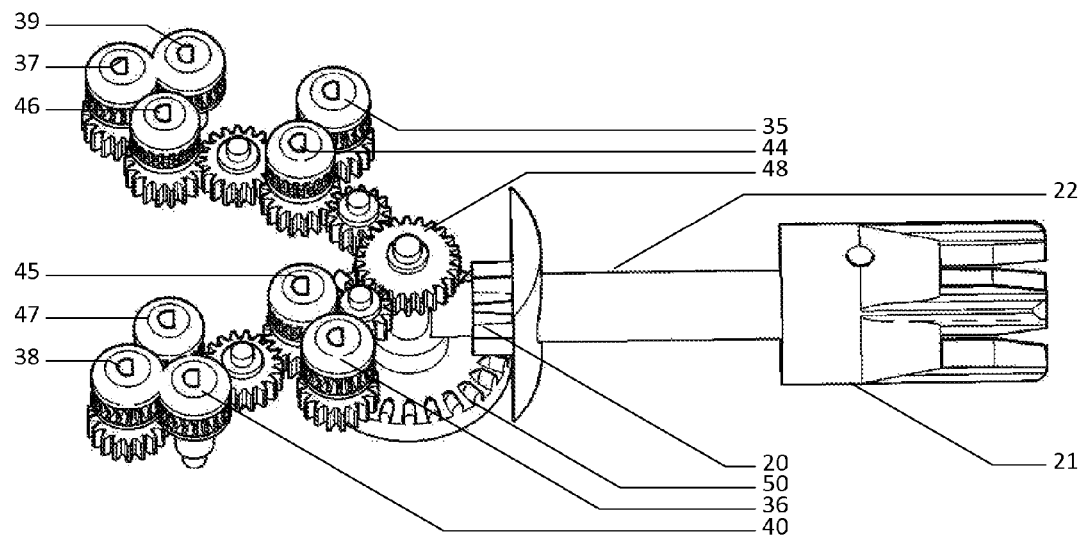
FIG. 9 shows an isometric view of the internal working mechanism of the suturing head of the suturing device of FIG. 1.
Figure 10:
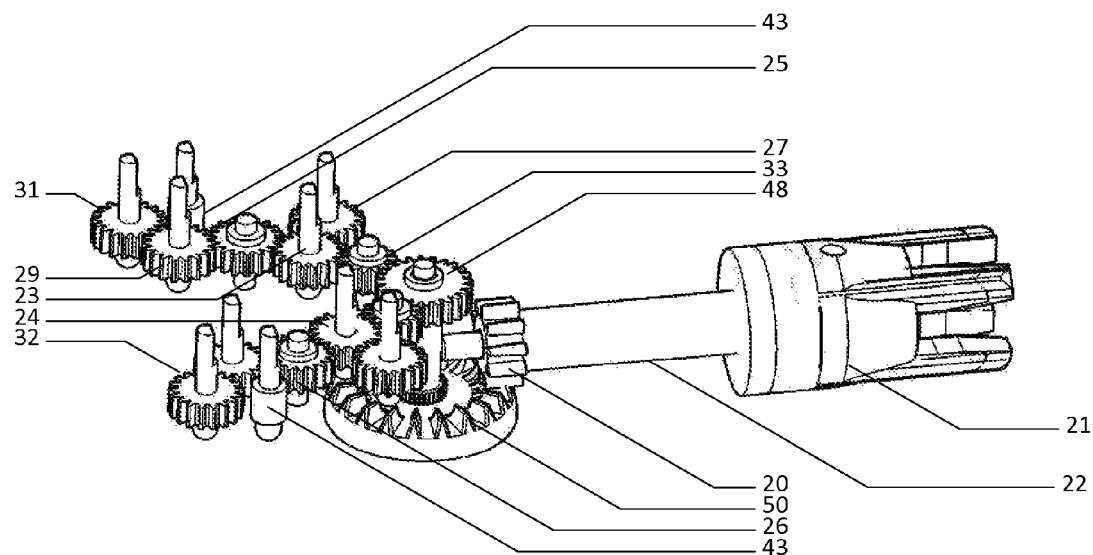
FIG. 10 shows an isometric view of the gearing mechanism only of the suturing head of the suturing device of FIG. 1.
Figure 11:
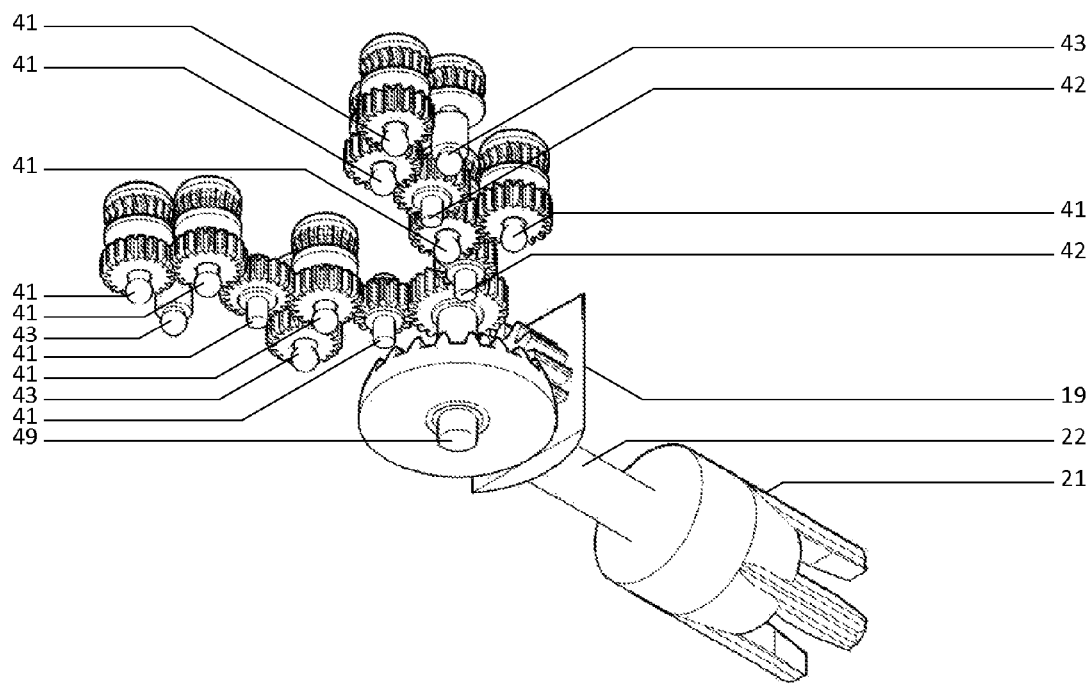
FIG. 11 shows an isometric underside view of the internal working mechanism of the suturing head of the suturing device of FIG. 1.
Figure 12:
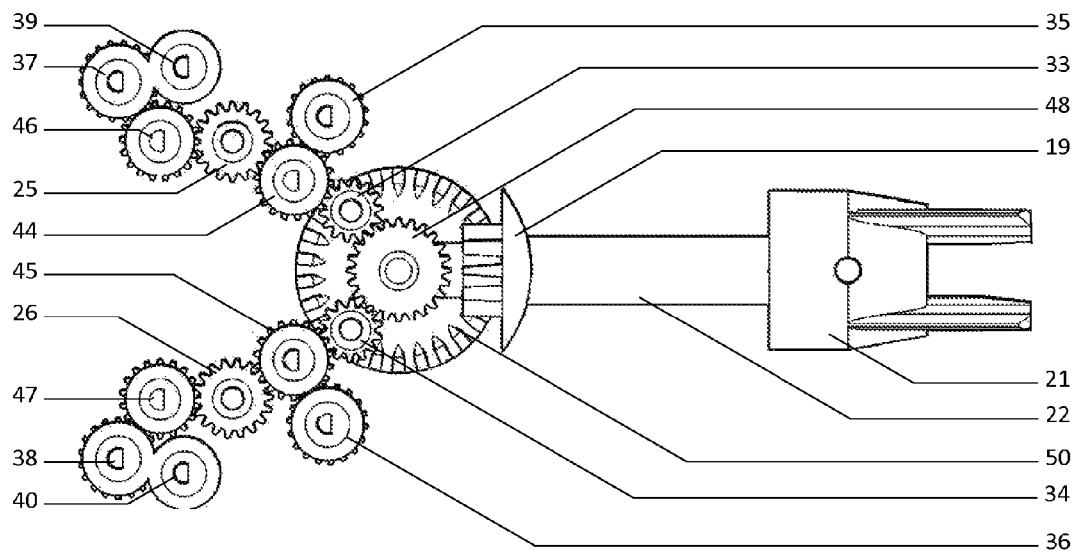
FIG. 12 shows a top view of the internal working mechanism of the suturing head of the suturing device of FIG. 1.
Figure 13:
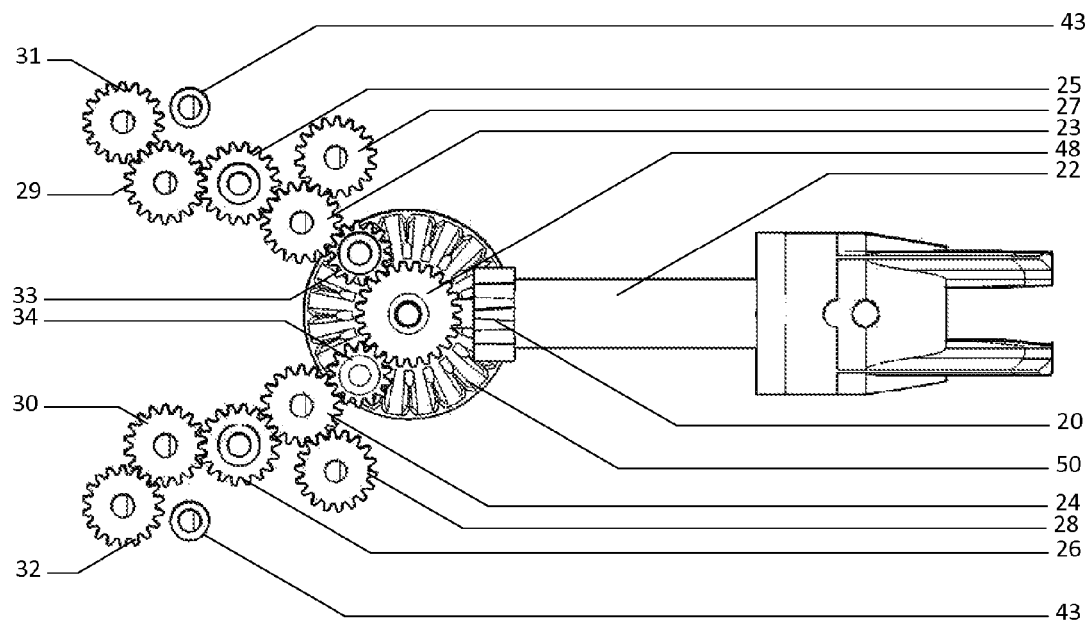
FIG. 13 shows a top view of the gearing mechanism only of the suturing head of the suturing device of FIG. 1.
Figure 14:
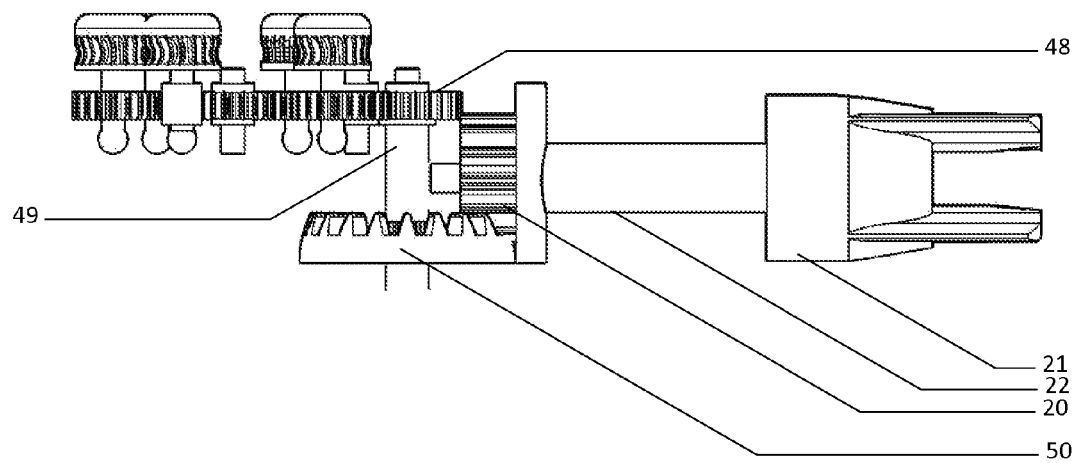
FIG. 14 shows an isometric view of a free standing roller and shaft of the suturing device of FIG. 1.

As shown in FIGS. 1 and 2, the suturing device 1 comprises a handle 2 and a replaceable suturing head 3. The suturing device 1 with the suturing head 3 removed is shown in FIGS. 3 and 4.

The handle 2 is shown in more detail in FIGS. 27 to 30. The handle 2 contains a control assembly comprising a drive motor 10, a control switch 8, a power cell 11 and secondary button 9. The control assembly controls a drive interface 15, which engages with a drive coupling 21 of the suturing head 3 as described later below.

The suturing head 3 comprises a suturing portion 4, a rotating section 5, a replaceable needle cartridge 6 and a stem 13. The suturing head 3 with the needle cartridge 6 removed is shown in FIG. 4.

The suturing head 3 is shown in detail in FIGS. 5 to 8. The rotating section 5 which includes a substantially semi-circular (or "U-shaped") portion containing the needle cartridge 6, which holds a suturing needle 16 as described in more detail below. As shown in FIGS. 21 to 24, an open groove 56 along the centre of the needle cartridge 6 results in an opening at either end of the needle cartridge 6. The opening at the re-entry end of the cartridge is surrounded by a cone shaped indentation 58. Also at the re-entry end of the cartridge 6 there is a thread guide 55 protruding from the chamfered side 57 of the open groove 56, to allow for the suture (not shown) to be guided to the outside of the needle cartridge 6 during rotation of the needle 16.

The internal components of the suturing head 3 are shown in FIGS. 9 to 14. As mentioned above, the stem 13 contains a drive coupling 21, which is driven by the corresponding drive interface 15 of the handle 2. The drive coupling 21 is attached to a drive shaft 22. The drive shaft 22 ends in a spur gear 20 which engages a crown gear 50 which is mounted on a shaft 49 which has mounted at the top a large cog 48 with the same axis. In alternative embodiments, the transfer of direction of drive achieved by the combination of the spur gear 20 and crown gear 50 may be achieved by any other means of mechanical kinetic motional translation such as bevel or worm gears.

The large cog 48 engages with reduction cogs 33 and 34 each mounted on a fixed shaft 42. Reduction cogs 33 and 34 further engage with drive cogs 23 and 24 mounted on a cog shaft with a spherical base 41. Each of these shafts is also mounted with drive rollers 44 and 45 respectively. Drive cogs 23 and 24 further engage with drive cogs 25 and 26 respectively each mounted on a fixed shaft 42. Drive cogs 23 and 24 also further engage with drive cogs 27 and 28 respectively mounted on a cog shaft with a spherical base 41. Each of these shafts is also mounted with outer rollers 35 and 36 respectively. Drive cogs 25 and 26 further engage with drive cogs 29 and 30 respectively each mounted on a fixed shaft 42. Each of these shafts is also mounted with drive rollers 46 and 47 respectively. Drive cogs 29 and 30 also further engage with drive cogs 31 and 32 respectively mounted on a cog shaft with a spherical base 41. Each of these shafts is also mounted with outer rollers 37 and 38 respectively. Outer rollers 39 and 40 are each mounted on an independent shaft with spherical base 43.

Figure 15:
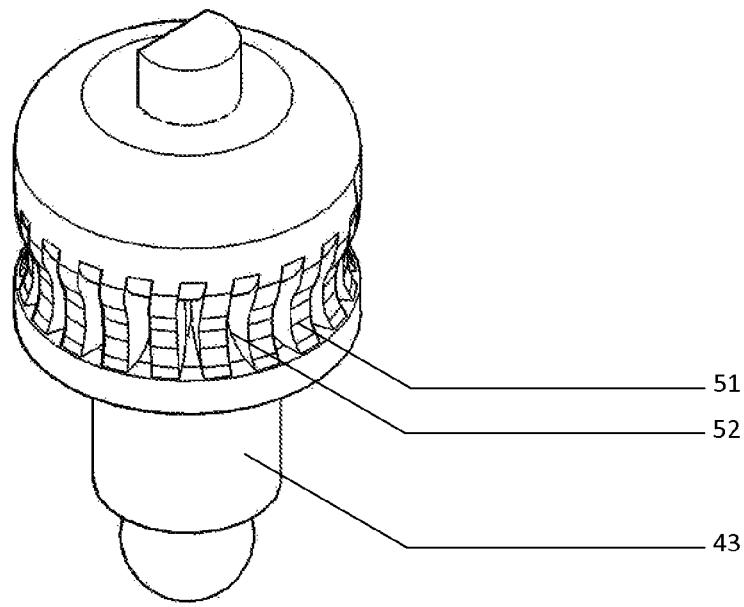
FIG. 15 shows a side view of the gearing mechanism only of the suturing head of the suturing device of FIG. 1.
Figure 16:
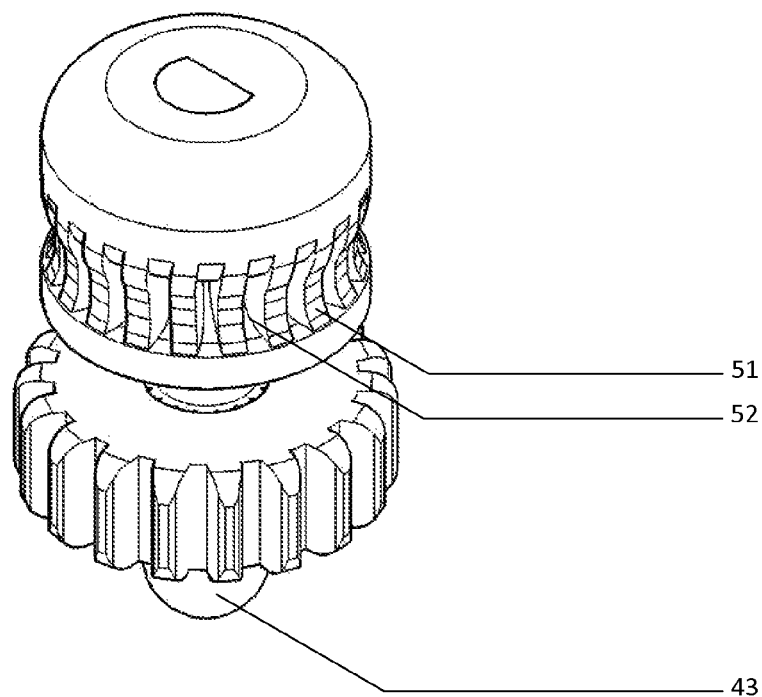
FIG. 16 shows an isometric view of the driven roller and corresponding gear and shaft of the suturing device of FIG. 1.
Figure 17:
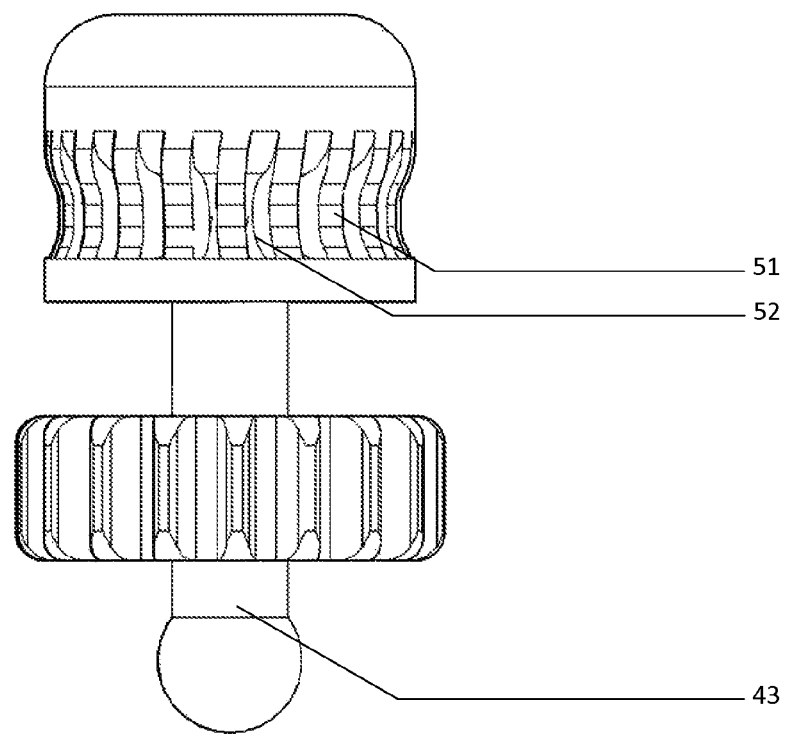
FIG. 17 shows a side view of the driven roller and corresponding gear and shaft of the suturing device of FIG. 1.
Figure 18:
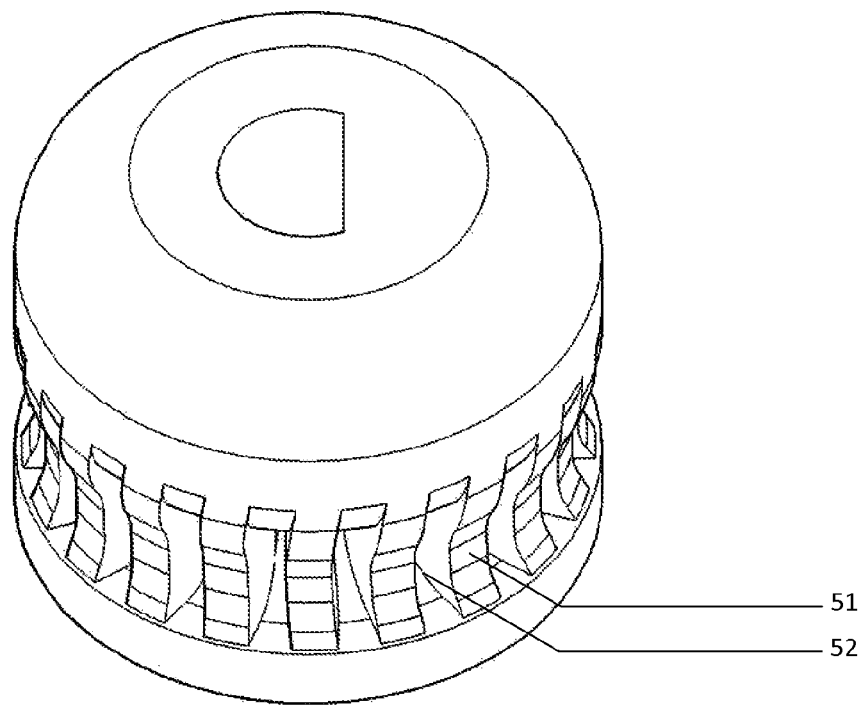
FIG. 18 shows an isometric view of the driven roller only of the suturing device of FIG. 1.

The mounting of the cogs and rollers on the shafts is shown in more detail in FIGS. 15 to 17.

The drive rollers 44, 45, 46, 47 and outer rollers 35, 36, 37, 38, 39, 40 are of a same design though sized proportionally to correspond with the difference in diameter between the inner and outer diameter of the needle. A roller is shown in more detail in FIG. 18. The roller has a series of rib-like drive surfaces 51 formed by slotted recesses 52 extending inwardly from the drive surface 53 of rollers. The curvilinear drive surfaces 51 are incurvate and undulant on the axis of rotation of the rollers, so that the drive surface 53 curves inwardly towards the axis of the roller between the top and bottom of the roller. The recesses 52 extend from between the drive surface 53, tapering to the root diameter of the roller, so that they are roughly triangular in shape.

In an alternative embodiment, the roller has a V-shaped groove in which the needle is held. In another alternative embodiment, the roller has a groove containing teeth that grip the needle. In another alternative embodiment, the roller is made of a porous material, and has a coating of a rubber material to grip the needle.

Figure 25:
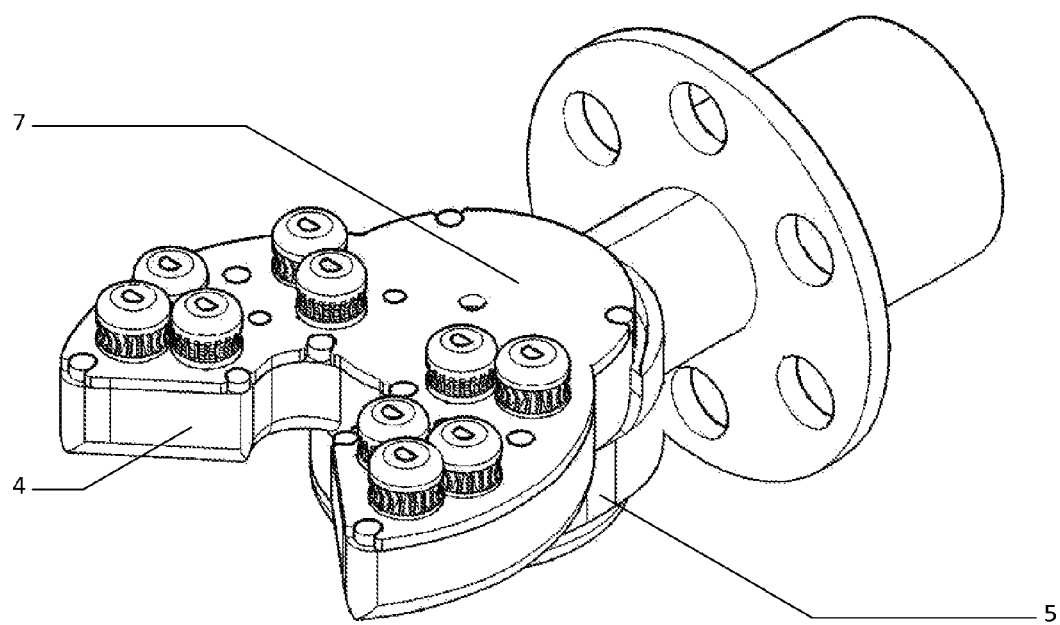
FIG. 25 shows an isometric view of the suturing head without the needle cartridge of the suturing device of FIG. 1.
Figure 26:
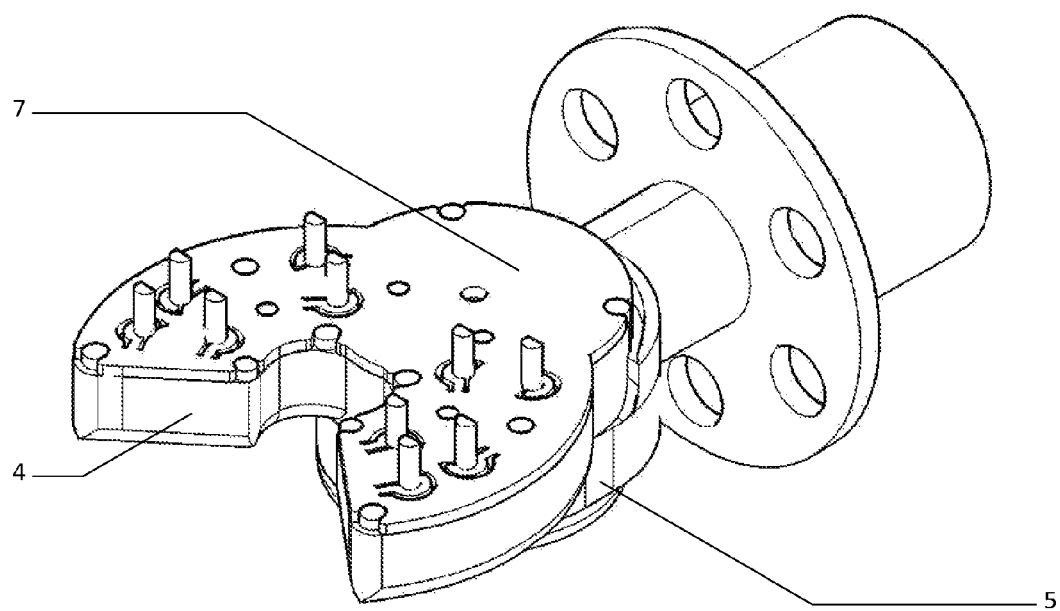
FIG. 26 shows an isometric view of the suturing head without the needle cartridge and without the rollers of the suturing device of FIG. 1.
Figure 27:
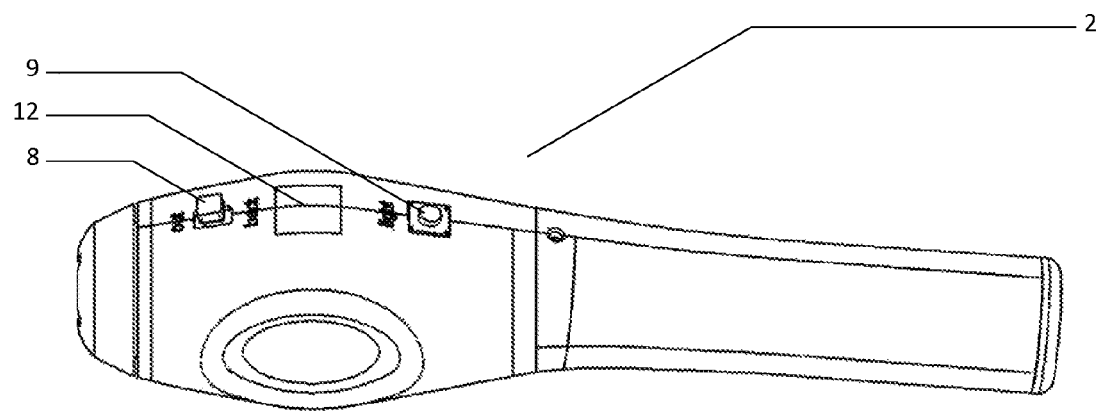
FIG. 27 shows an isometric view of the handle of the suturing device of FIG. 1.
Figure 28:
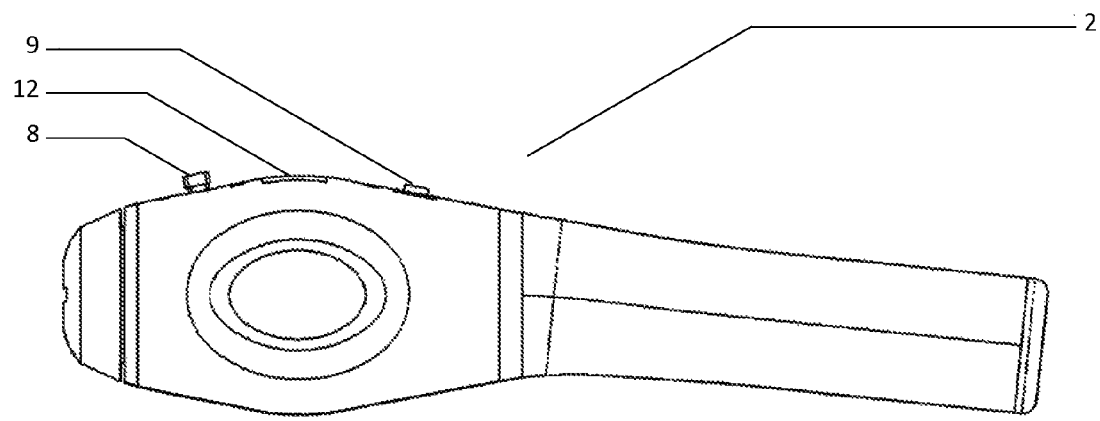
FIG. 28 shows a side view of the handle of the suturing device of FIG. 1.
Figure 29:
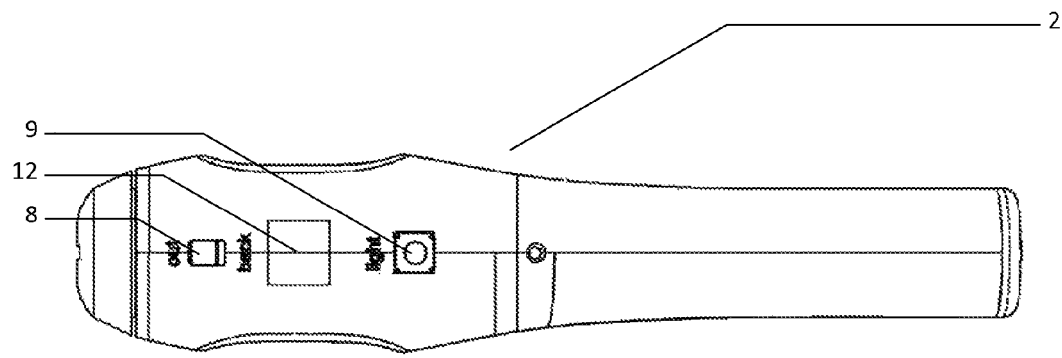
FIG. 29 shows a top view of the handle of the suturing device of FIG. 1.
Figure 30:
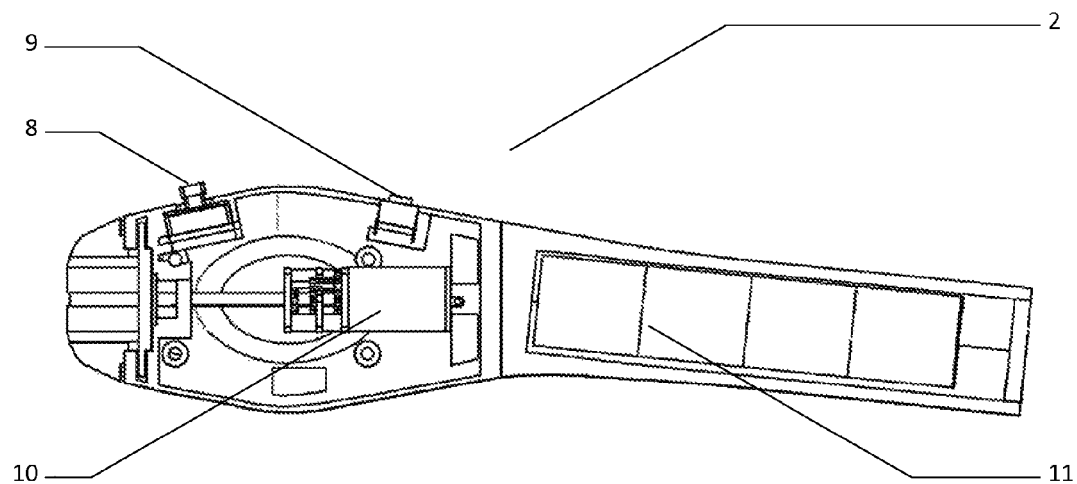
FIG. 30 shows a cross-section view of the handle of the suturing device of FIG. 1.
Figure 31:
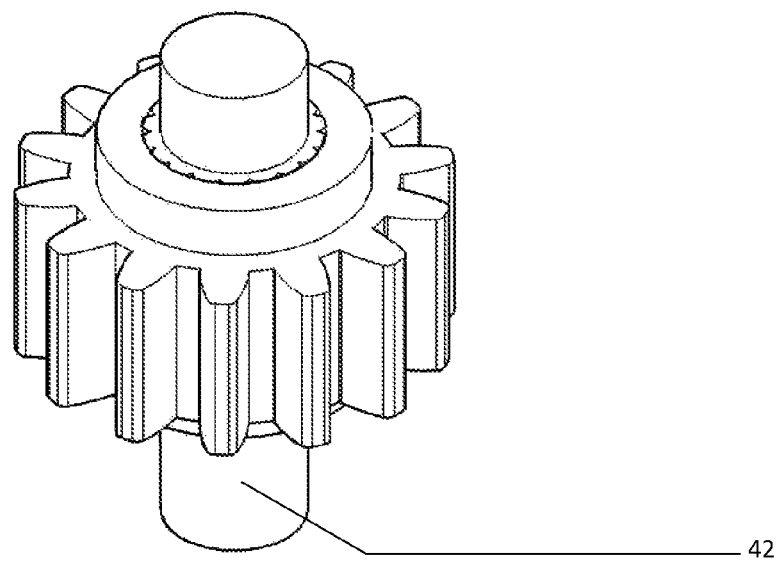
FIG. 31 shows an isometric view of the straight shafted intermediate gear of the suturing device of FIG. 1.
Figure 32:
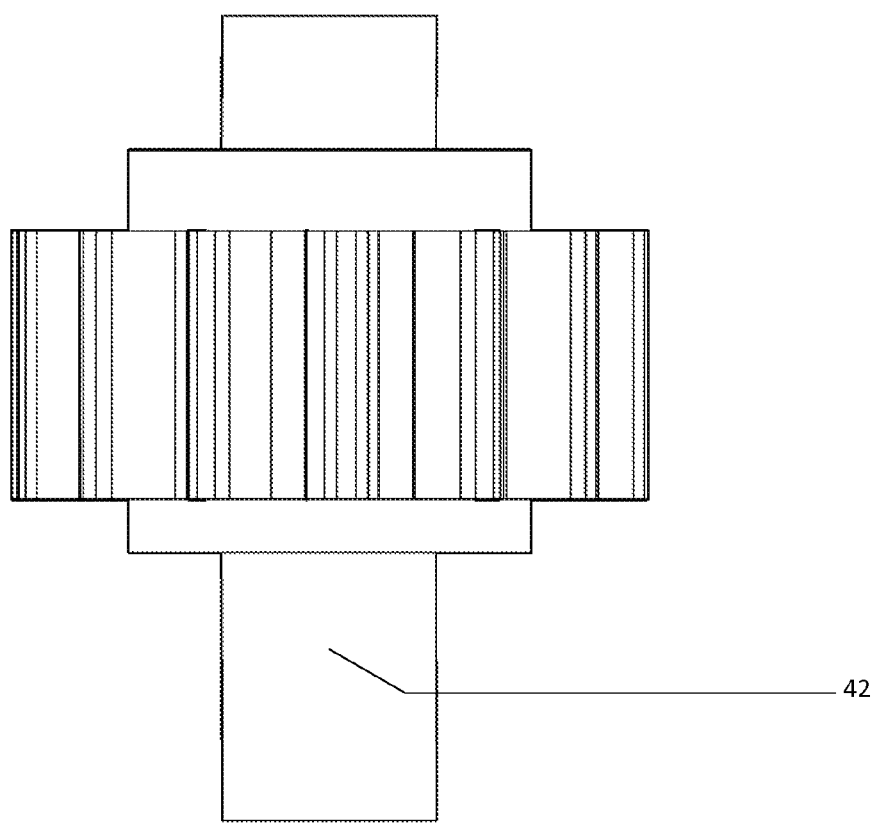
FIG. 32 shows a side view of the straight shafted intermediate gear of the suturing device of FIG. 1.
Figure 33:
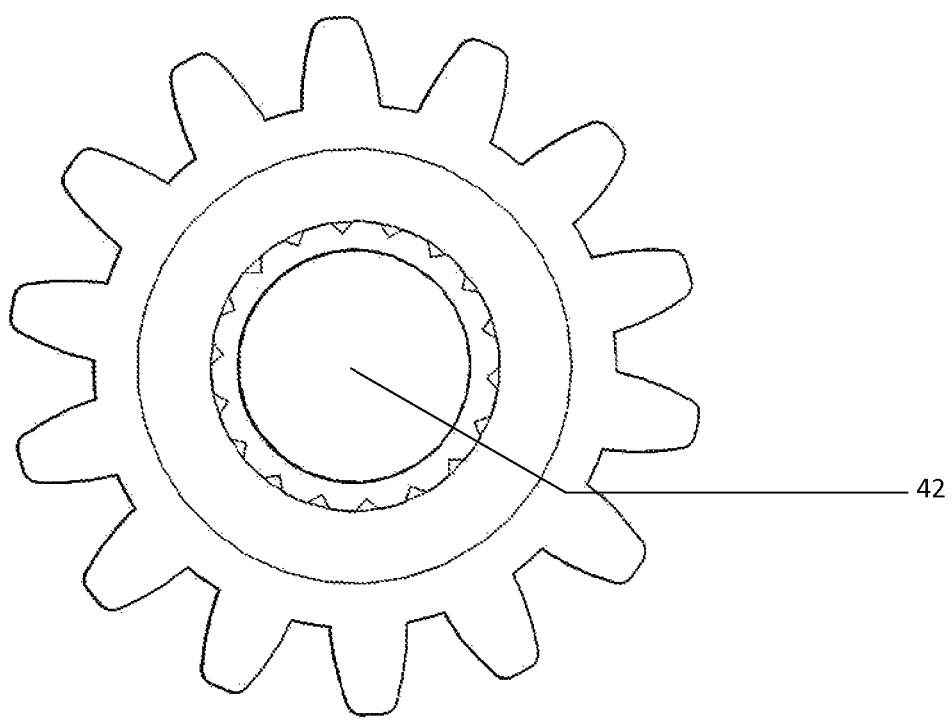
FIG. 33 shows a top view of the straight shafted intermediate gear of the suturing device of FIG. 1.
Figure 34:
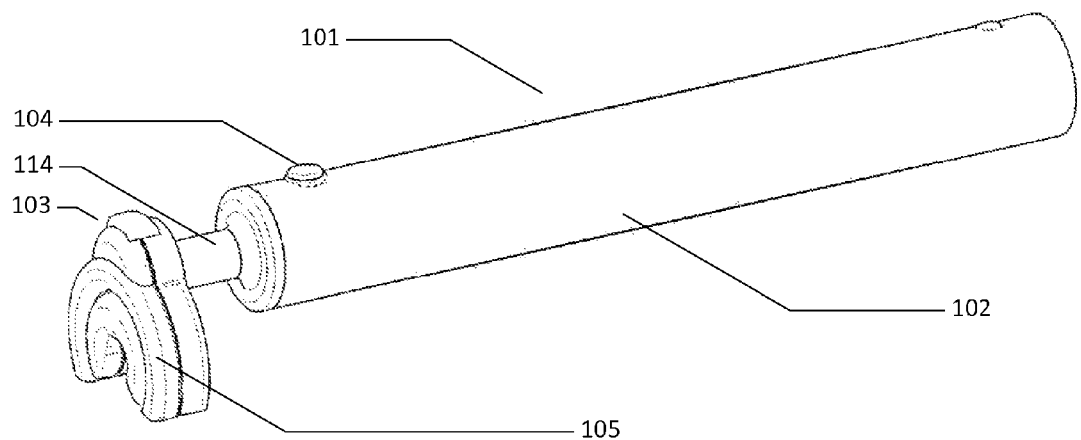
FIG. 34 shows an isometric view of a suturing device according to another embodiment of the invention.

The suturing head 5 without the needle cartridge 6 is shown in detail in FIGS. 25 and 26. The suturing head 5 comprises a spring plate 7, which is shown in detail in FIGS. 19 and 20. The spring plate 7 is made of laser-etched steel of thickness 0.1 mm. The spring plate 7 comprises a plurality of cuts to form shaft springs 65. The spring plate 7 is positioned in the suturing head 5 so that each cog shaft with a spherical base 41 passes through and is retained by a shaft spring 65. The spherical base 41 of each cog shaft is seated in a shaft bore hole in the suturing portion 4 which allows the shaft to pivot with respect to the axis of the shaft. This action allows the opposite or triangularly placed drive rollers and outer rollers mounted on their corresponding cog shaft with a spherical base 41 to move perpendicular to the needle 16 and allows for the passage of the tapered and non-tapered section of the needle between the opposite or triangularly placed drive and outer rollers, while the shaft spring 66 allows for mechanical tension that acts to increase the grip upon the needle by opposite or triangularly placed drive and outer rollers.

The drive rollers 44, 45, 46, 47 are arranged so that the diametrically interior surface of the curved suturing needle 16, which lies in the open groove 56 of the needle cartridge 6, engages with the traction band 53 at the centre of the drive surfaces 51 and 52 of the drive roller.

The outer rollers 35, 36, 37, 38, 39, 40 are arranged so that the diametrically exterior surface of the curved suturing needle 16, which lies in the open groove 56 of the needle cartridge 6, engages with the traction band 53 at the centre of the drive surfaces 51 and 52 of the outer roller. In particular, outer rollers 37 and 39 are arranged opposite drive roller 46 in a triangular arrangement. Outer rollers 38 and 40 are arranged opposite drive roller 47 in a triangular arrangement. Outer roller 35 is arranged opposite drive roller 44 and outer roller 36 is arranged opposite drive roller 45.

The needle cartridge 6 is shown in detail in FIGS. 21 to 24. The needle cartridge 6 holds a curved suturing needle 16 with a thread (not shown) extending from the non-tapered end of the needle in an open groove 56. The thread is guided out of the body of the cartridge during use by the thread guide 55 on re-entry of the needle into the open groove 56 of needle cartridge 6, and held out of the body of the cartridge by the chamfered side 57 of the open groove 56. The needle cartridge is inserted into and removed from the suturing head 3 by depressing the finger tabs 59 and 60. The open groove 56 in cross-section consists of a major arc that retains the needle 16 within the body of the needle cartridge 6 whilst allowing the thread to stay extended to the exterior of the needle cartridge.

The indentations 61, 62, 63 and 64 on the underside of the needle cartridge 6 allow for the drive rollers 44, 45, 46 and 47 and outer rollers 35, 36, 37, 38, 39 and 40 to protrude into the needle cartridge 6 to allow drive to the needle 16.

In use, the suturing portion 4 is rotated about the rotating section 5 to the desired position for use. The user depresses the secondary button 9 in the control assembly to activate the LED light that originates in the handle 2 and travels through a series of light apertures 18 to light the working area.

Following the positioning of the rotating section 5 the control assembly is controlled by a user by means of the control switch 8 and the control assembly in turn operates the device by means of the drive interface 15. The drive interface 15 engages with the drive coupling 21 which is attached to the drive shaft 22 which ends in a spur cog 20 which causes the crown gear 50, and thus the large cog 48, to move. The large cog 48 engages with reduction cogs 33 and 34 each mounted on a fixed shaft 42. Reduction cogs 33 and 34 further engage with drive cogs 23 and 24 mounted on a cog shaft with a spherical base 41. Each of these shafts is also mounted with drive rollers 44 and 45 respectively. Drive cogs 23 and 24 further engage with drive cogs 25 and 26 respectively each mounted on a fixed shaft 42. Drive cogs 23 and 24 also further engage with drive cogs 27 and 28 respectively mounted on a cog shaft with a spherical base 41. Each of these shafts is also mounted with outer rollers 35 and 36 respectively. Drive cogs 25 and 26 further engage with drive cogs 29 and 30 respectively each mounted on a fixed shaft 42. Each of these shafts is also mounted with drive rollers 46 and 47 respectively. Drive cogs 29 and 30 also further engage with drive cogs 31 and 32 respectively mounted on a cog shaft with a spherical base 41. Each of these shafts is also mounted with outer rollers 37 and 38 respectively. Thus, the rotation of the drive rollers 44, 45, 46 and 47 and the outer rollers 35, 36, 37 and 38 causes the suturing needle 16 to rotate around a circular path incorporating the open groove 56 of the needle cartridge 6 by means of the friction provided by the traction band 53 of the drive rollers and outer rollers and under tension provided by the shaft springs 65 of the spring plate 7, with additional rotational stability provided by outer rollers 39 and 40 also under tension from shaft springs 65 of the spring plate 7.

The suturing needle 16 is at all times held in alignment in the circular path regardless of its position in the circular path, as in all positions it will be held by the curvilinear drive surfaces 51 and 52 of at least two outer rollers in the correct position within the traction band 53 of the corresponding drive rollers. The parts of the drive surfaces 51 and 52 of the drive rollers and outer rollers above and below the traction band 53 of the curvilinear surface that engages with the diametrically interior surface of the curved needle thus act to prevent the suturing needle 16 rotating about its centre and so moving out of alignment with the circular path. The triangular arrangement of the drive rollers 46 and outer rollers 37 and 39 in particular act to hold the suturing needle 16 in alignment even when it is almost completely outside the semi-circular portion of the suturing portion 4 and needle cartridge 6.

Should the suturing needle 16 nevertheless be moved out of alignment when any portion of it is outside the semi-circular portion of the suturing portion 4 and needle cartridge 6, for example because the suturing needle is passing through particularly dense or hardened tissue, when re-entering the suturing portion 4 and the needle cartridge 6 the tip of the suturing needle 16 will be guided by the cone shaped indentation 58 at the first end of the needle cartridge 6 back into the correct alignment.

In use, the suturing needle 16 will of course be being used to suture using suturing thread. During suturing, the suture thread is able to pass through the open groove 24 to rotate outside of the constraints of the semi-circular portion of needle cartridge 6, thus allowing the device to be used for suturing without the device being attached to the tissue being sutured.

The control assembly may be controlled by a user by means of the control switch 8 and secondary button 9 as follows. The user can push the control switch 8 forwards (towards the suturing head 3) to move the suturing needle 16 anti-clockwise, and backwards (away from the suturing head 3) to move the suturing needle 16 clockwise. Moving the control switch 8 a greater distance causes the suturing needle 16 to move at greater speed. Pressing the control switch 8 down, towards the handle 2 (i.e. "clicking" it) causes the suturing needle 16 to move in the direction previously engaged by the control switch 8 in one complete rotation around the circular path so that the needle 16 sits entirely within the body of the needle cartridge 6, thus completing one suture and, upon completion of the use of the suture within the body of the needle cartridge 6, allowing the needle cartridge 6 to be removed from the suturing head 3 and disposed of safely. The secondary button 9 is used to turn the LED light 7 on and off. However, the skilled person will appreciate that any other suitable control system could be used.

A suturing device in accordance with another embodiment of the invention is now described with reference to FIGS. 34 to 69.

Figure 35:
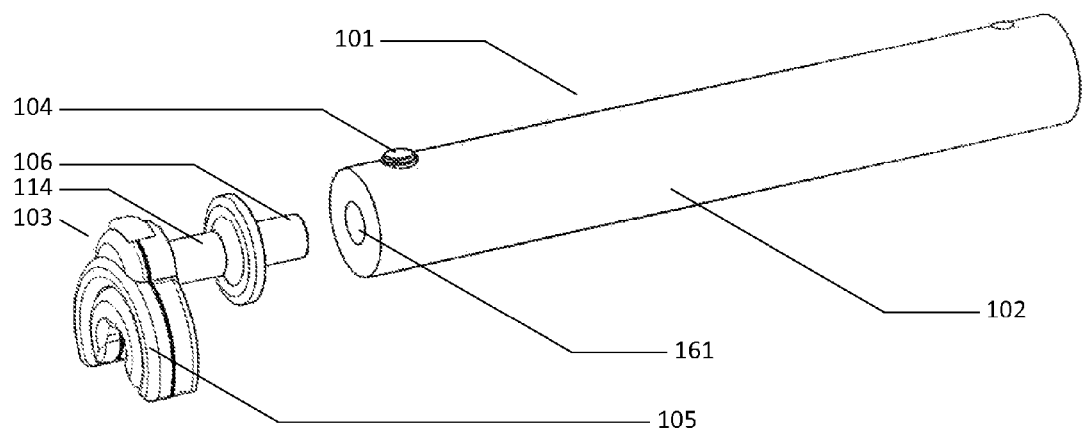
FIG. 35 shows an isometric view of the suturing device of FIG. 34 in two pieces.

As shown in FIGS. 34 to 39, the suturing device 101 comprises a handle 102 and a replaceable suturing head 103. The suturing device 101 with the suturing head 103 removed is shown in FIG. 35.

Figure 64:
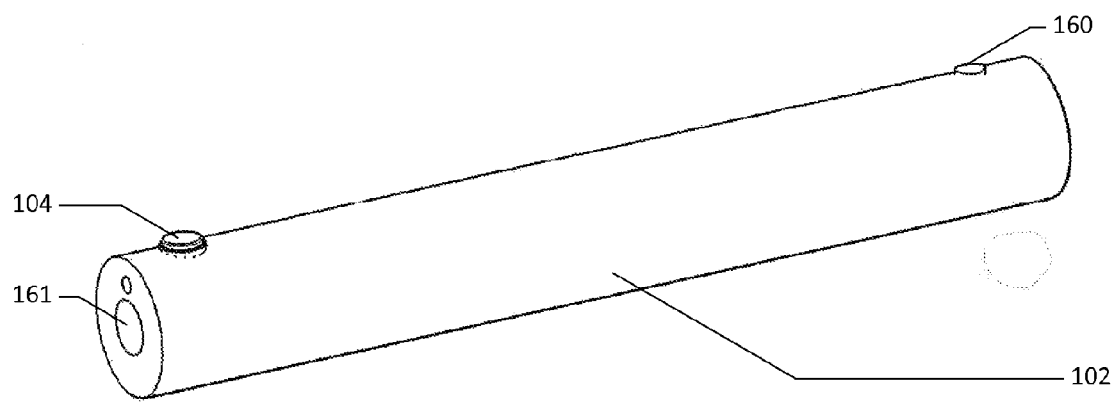
FIG. 64 shows an isometric view of the handle of the suturing device of FIG. 34.
Figure 65:
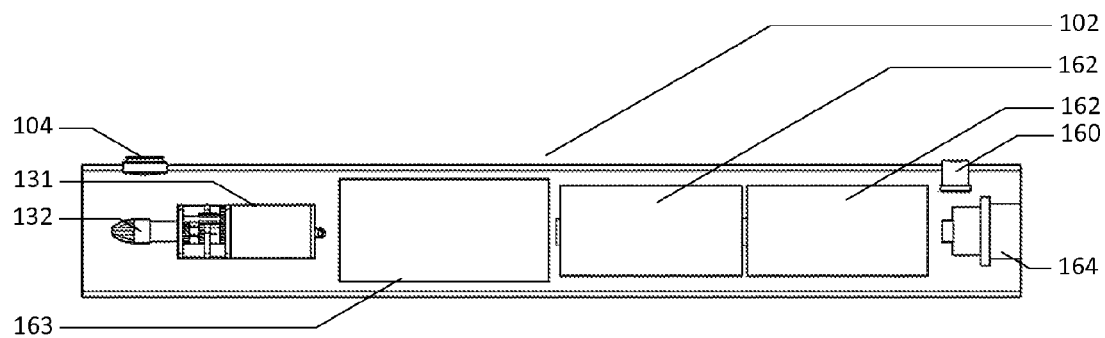
FIG. 65 shows a cross section side view of the handle of the suturing device of FIG. 34.
Figure 66:
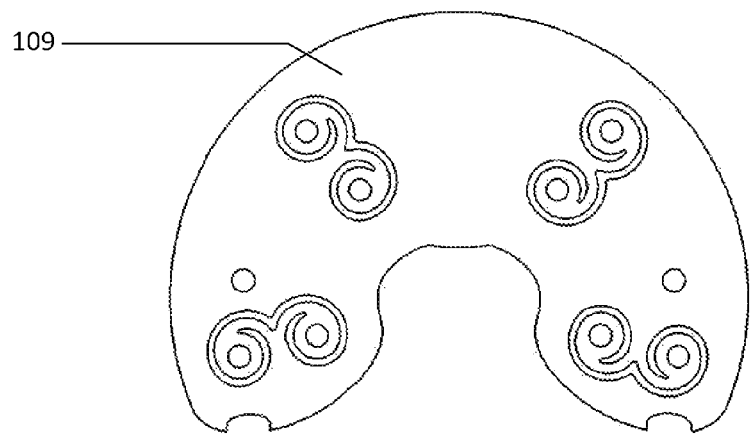
FIG. 66 shows a top view of a first example of the spring plate of the suturing device of FIG. 34.
Figure 67:
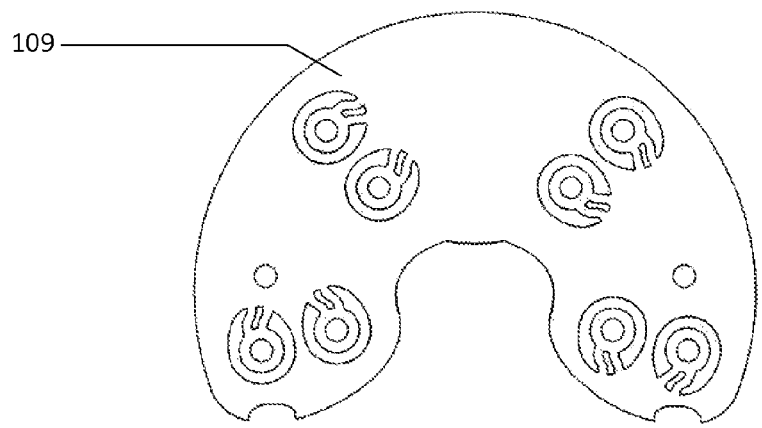
FIG. 67 shows a top view of another example of the spring plate of the suturing device of FIG. 34.
Figure 68:
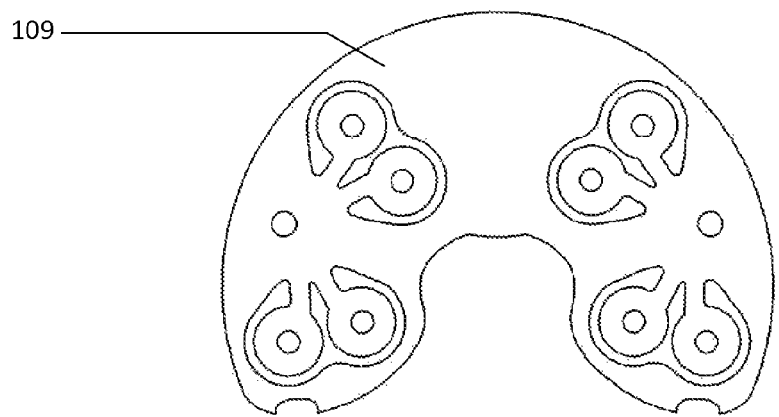
FIG. 68 shows a top view of another example of the spring plate of the suturing device of FIG. 34.
Figure 69:
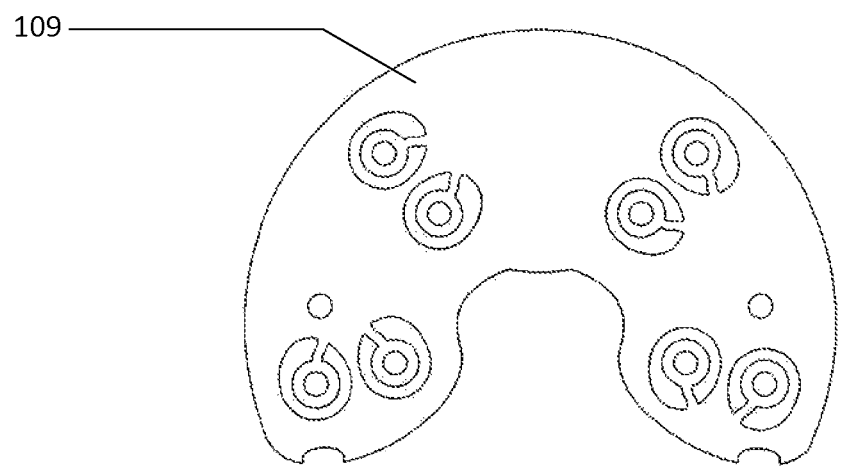
FIG. 69 shows a top view of another example of the spring plate of the suturing device of FIG. 34.

The handle 102 is shown in more detail in FIGS. 64 and 65. The handle 102 contains a control assembly comprising a drive motor 131, a control switch 104, a power cell or cells 162 and power button 160. The power cells 162 may be recharged through a power charge socket 164. The control assembly controls a drive coupling plug 132, which engages with a drive coupling socket 133 of the suturing head 103 as described later below.

Figure 37:
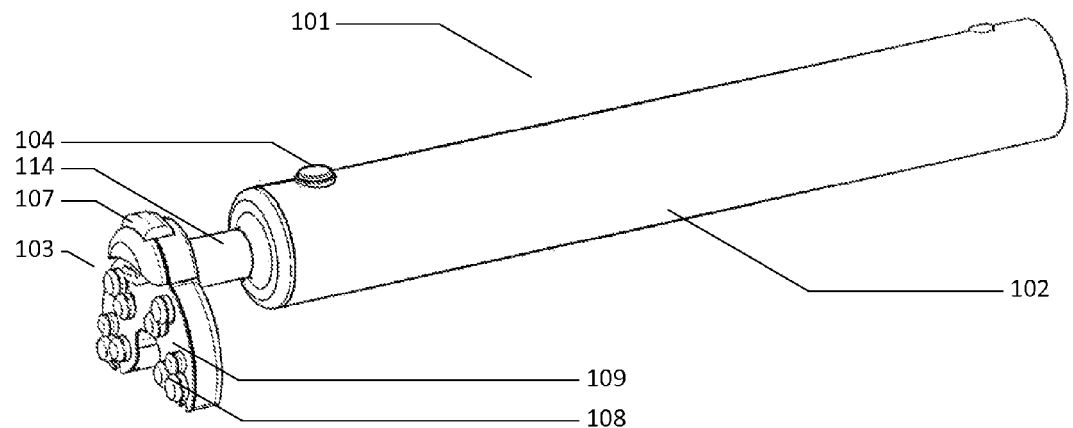
FIG. 37 shows an isometric view of the suturing device of FIG. 34 with the needle cartridge completely removed.
Figure 38:
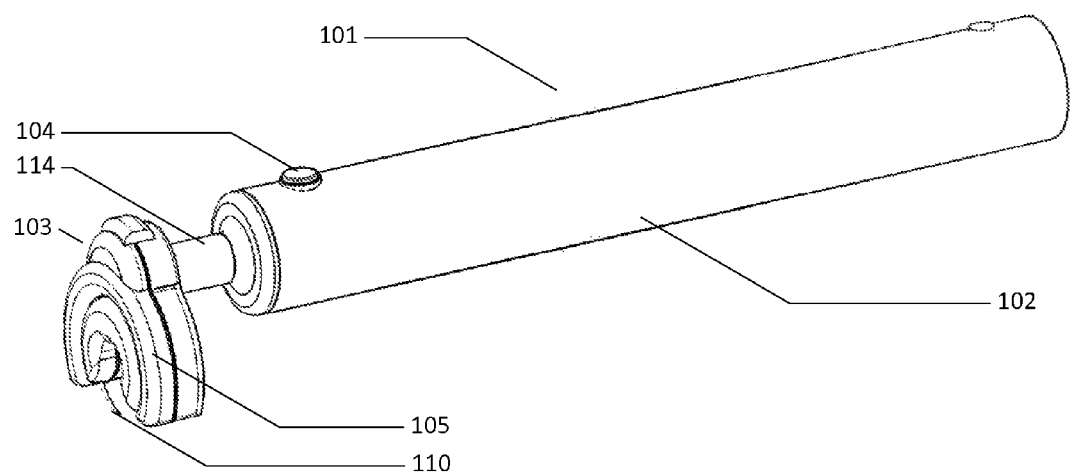
FIG. 38 shows an isometric view of the suturing device of FIG. 34 with the needle partly rotated.
Figure 39:
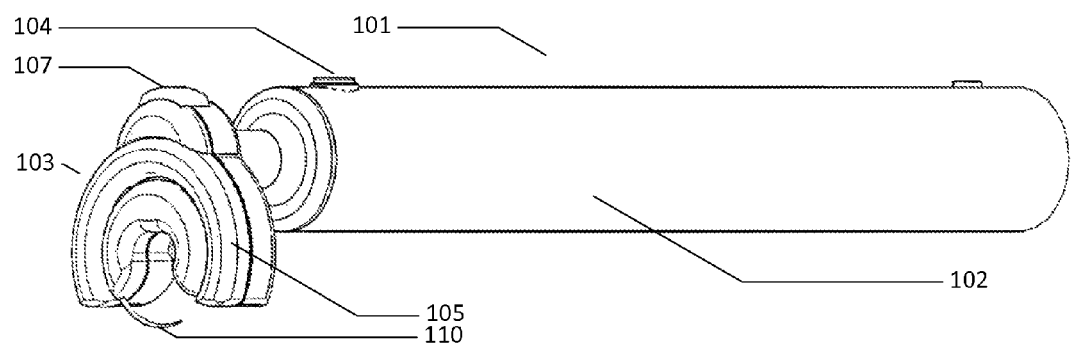
FIG. 39 shows an alternate view of the suturing device of FIG. 34 with the needle partly rotated.
Figures 40, 41:
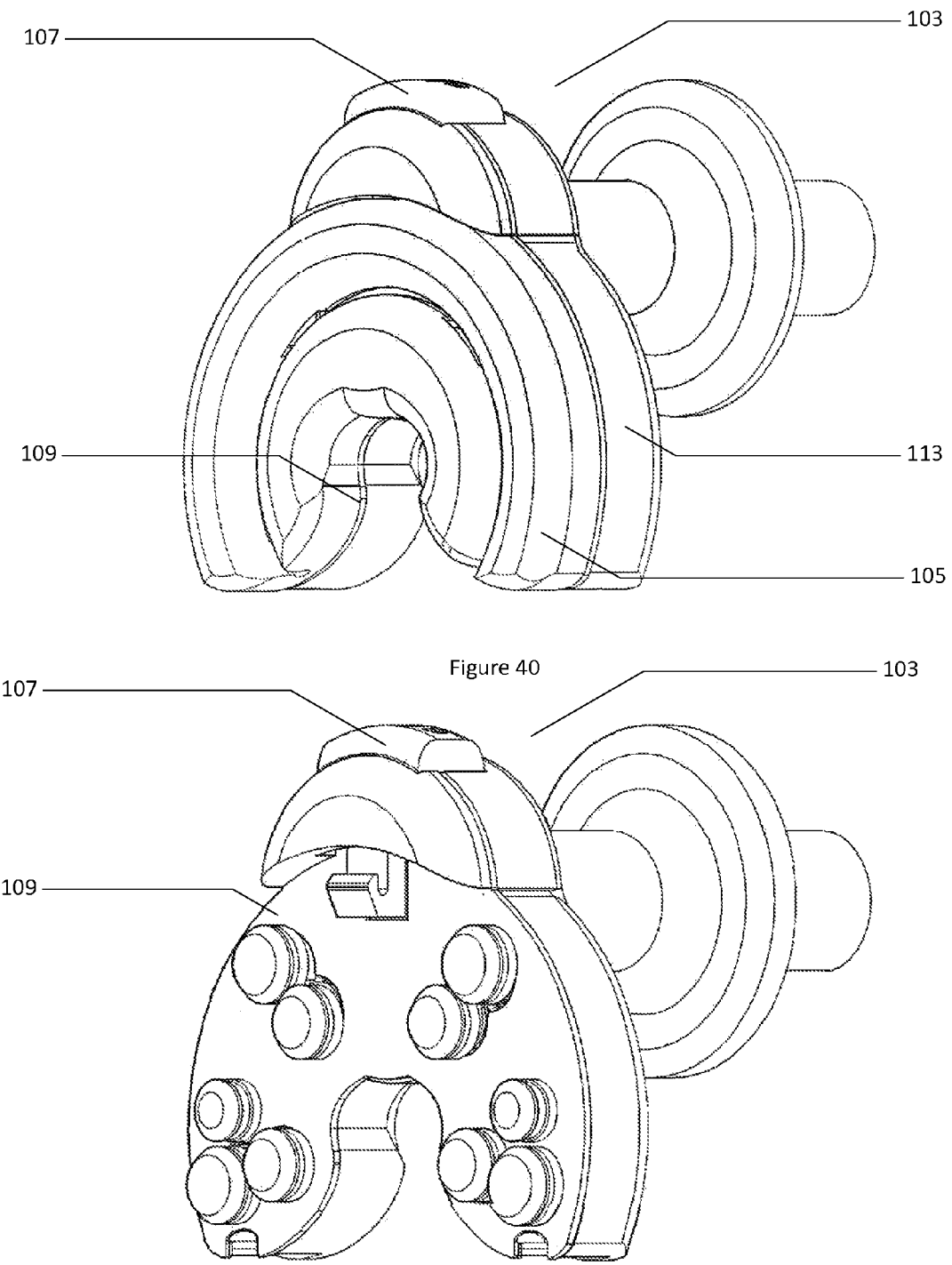
FIG. 40 shows a front view of the suturing head of the suturing device of FIG. 34.
FIG. 41 shows a front view of the suturing head of the suturing device of FIG. 34 with the needle cartridge removed.
Figure 42:
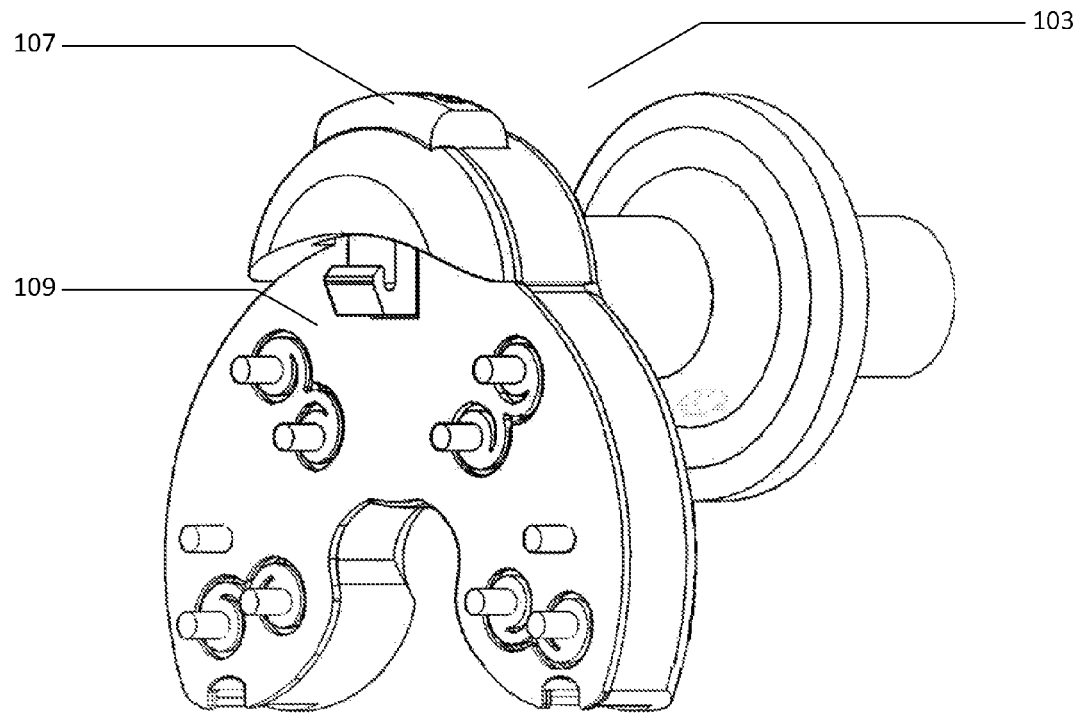
FIG. 42 shows a front view of the suturing head of the suturing device of FIG. 34 with the needle cartridge and drive rollers removed.
Figure 43:
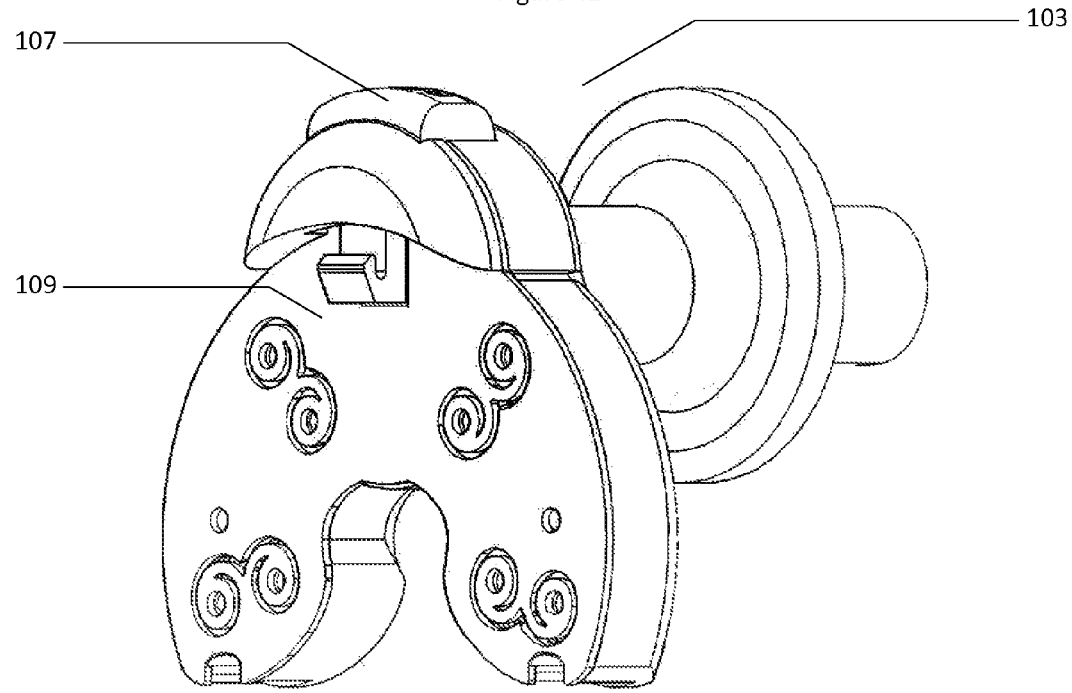
FIG. 43 shows a front view of the suturing head of the suturing device of FIG. 34 with the needle cartridge, drive rollers and shafts removed.
Figure 44:
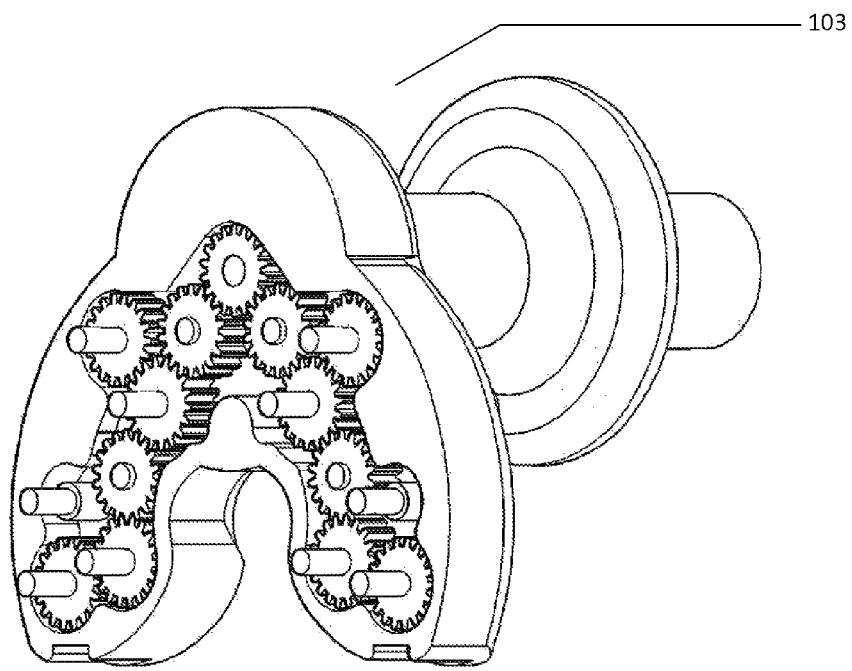
FIG. 44 shows a front view of the suturing head of the suturing device of FIG. 34 with the needle cartridge, drive rollers and spring plate removed.

The suturing head 103 comprises a head body 113, a stem 114 and a replaceable needle cartridge 15. The suturing head 103 with the needle cartridge 105 removed is shown in FIG. 37.

As shown for example in FIG. 35, the stem 114 of the suturing head 103 includes a head plug 106 that engages with a corresponding head stem socket 161 of the handle 102 to keep the suturing head 103 mounted upon the handle 102.

The suturing head 103 is shown in detail in FIGS. 40 to 44. The needle cartridge 105 attaches to the suturing head body 113. The suturing head body 113 and needle cartridge 105 are shaped so as to cover part of a circle. The needle cartridge 105, which holds a suturing needle 110 is described in more detail below. As shown in FIGS. 46 to 57, an open groove 115 along the centre of the needle cartridge 105 results in an opening at either end of the needle cartridge 105. The opening at the re-entry end of the cartridge has a cone shaped indentation 118.

Figure 45:
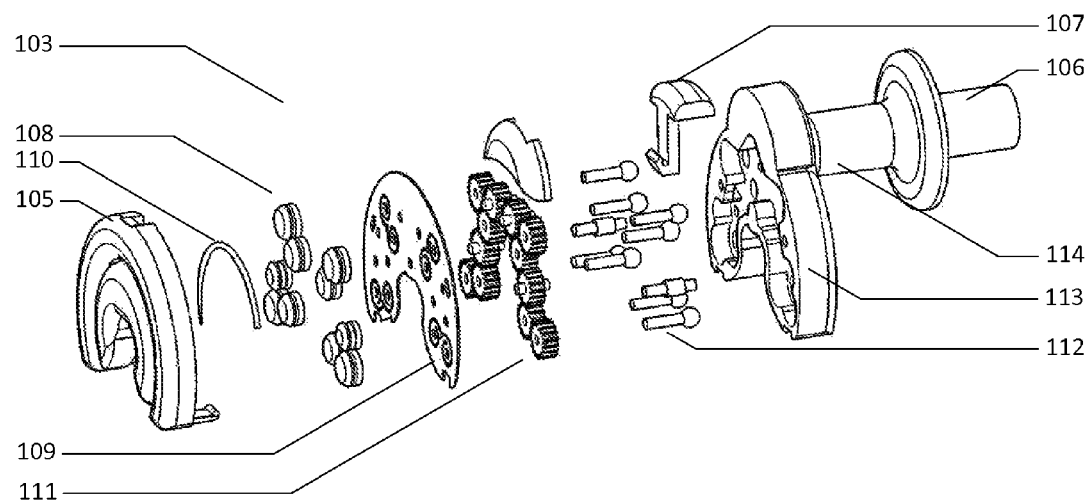
FIG. 45 shows an exploded view of the suturing head of the suturing device of FIG. 34.
Figure 46:
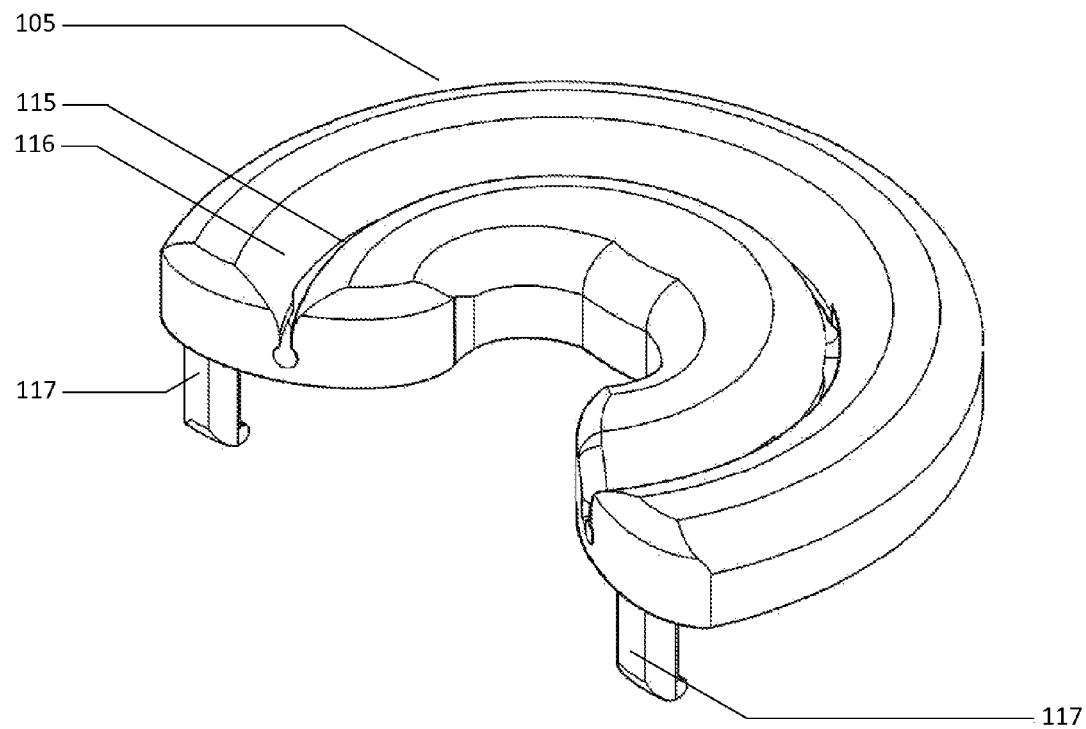
FIG. 46 shows an isometric top view of the needle cartridge of the suturing head of the suturing device of FIG. 34.
Figure 47:
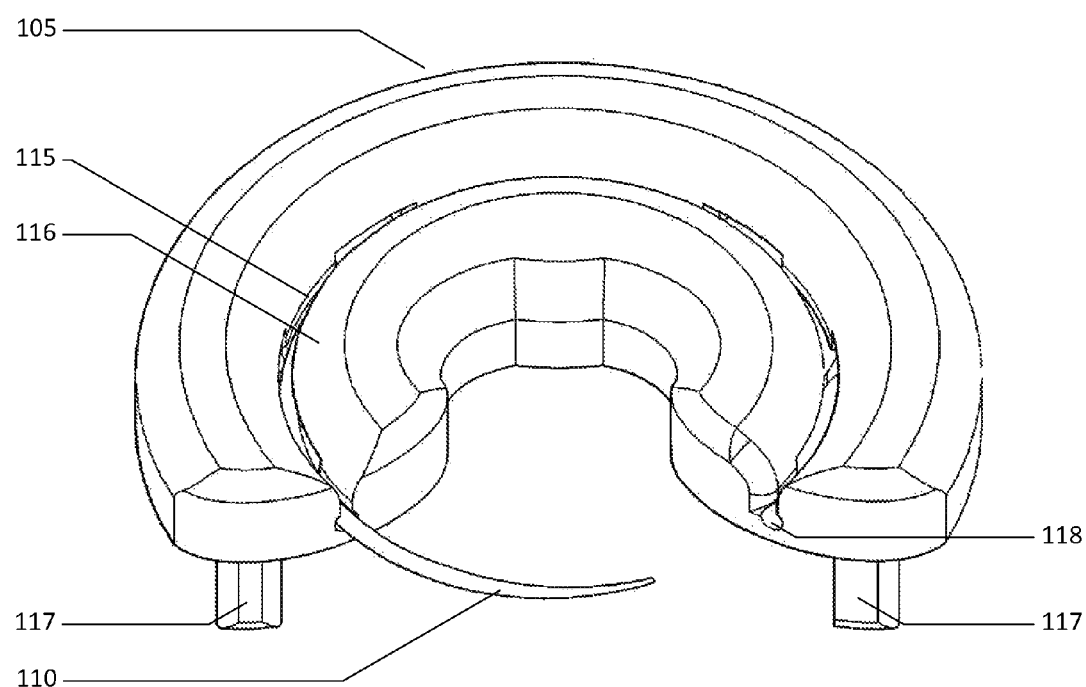
FIG. 47 shows a front top view of the needle cartridge of the suturing head of the suturing device of FIG. 34.
Figure 48:
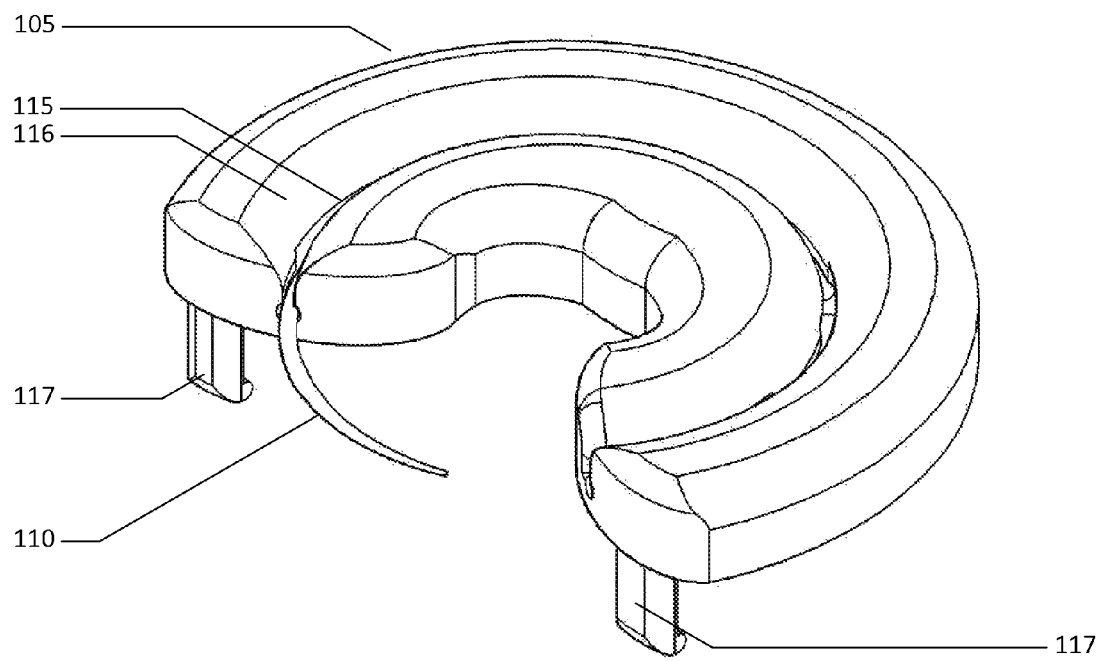
FIG. 48 shows an isometric top view of the needle cartridge of the suturing head of the suturing device of FIG. 34 with the needle partly rotated.
Figure 49:
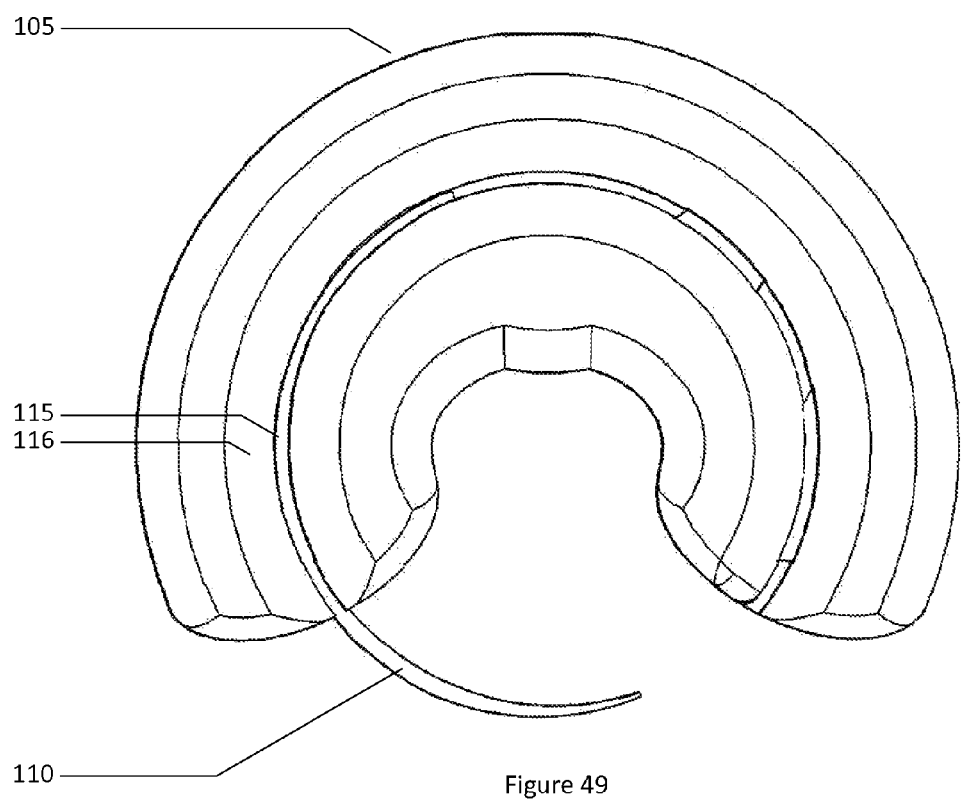
FIG. 49 shows a top view of the needle cartridge of the suturing head of the suturing device of FIG. 34 with the needle partly rotated.
Figure 50:
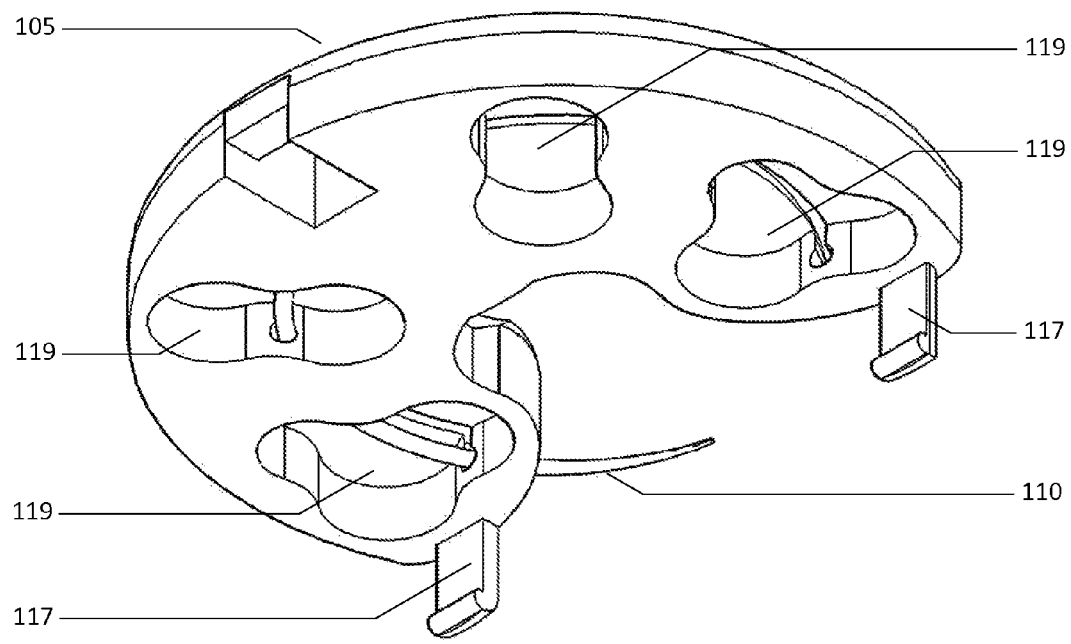
FIG. 50 shows an isometric underside view of the needle cartridge of the suturing head of the suturing device of FIG. 34 with the needle partly rotated.
Figure 51:
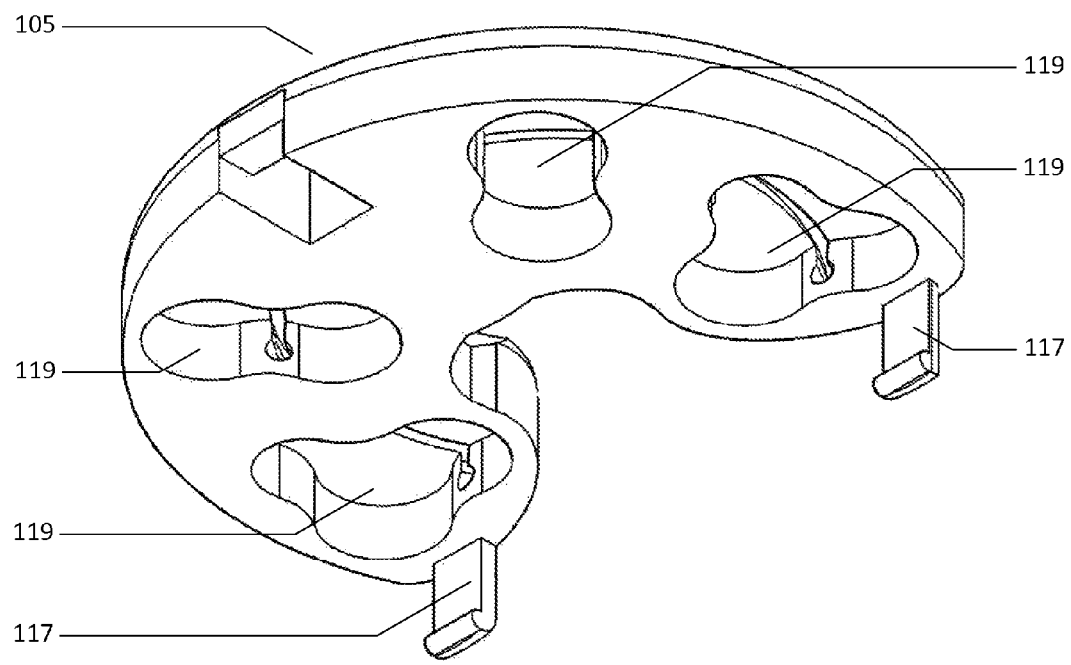
FIG. 51 shows an isometric underside view of the needle cartridge of the suturing head of the suturing device of FIG. 34.

The internal components of the suturing head 103 are shown in FIG. 45. As mentioned above, the stem 114 contains a drive coupling socket 133, which is driven by the corresponding drive coupling plug 132 of the handle 102. The drive coupling plug 132 is attached to a drive shaft 134. The drive shaft 134 ends in the main drive cog 135.

Figure 19:
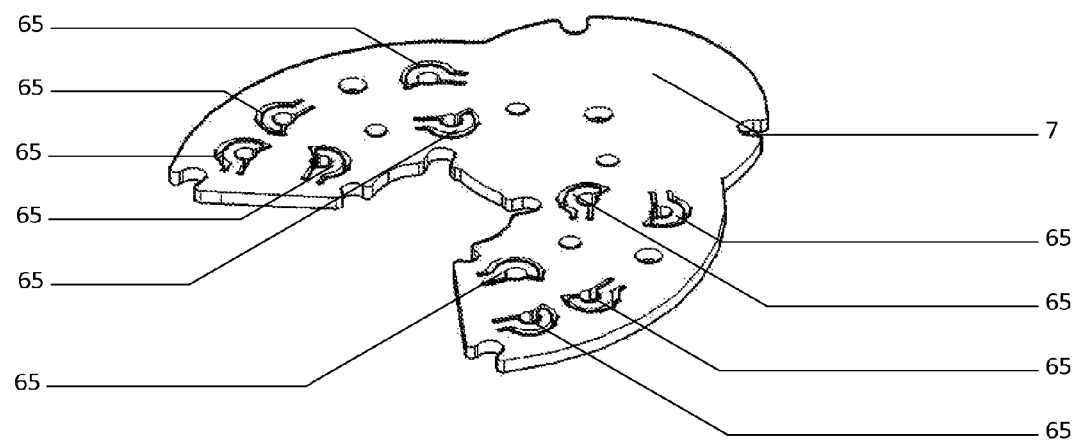
FIG. 19 shows an isometric view of the spring plate of the suturing device of FIG. 1.
Figure 20:
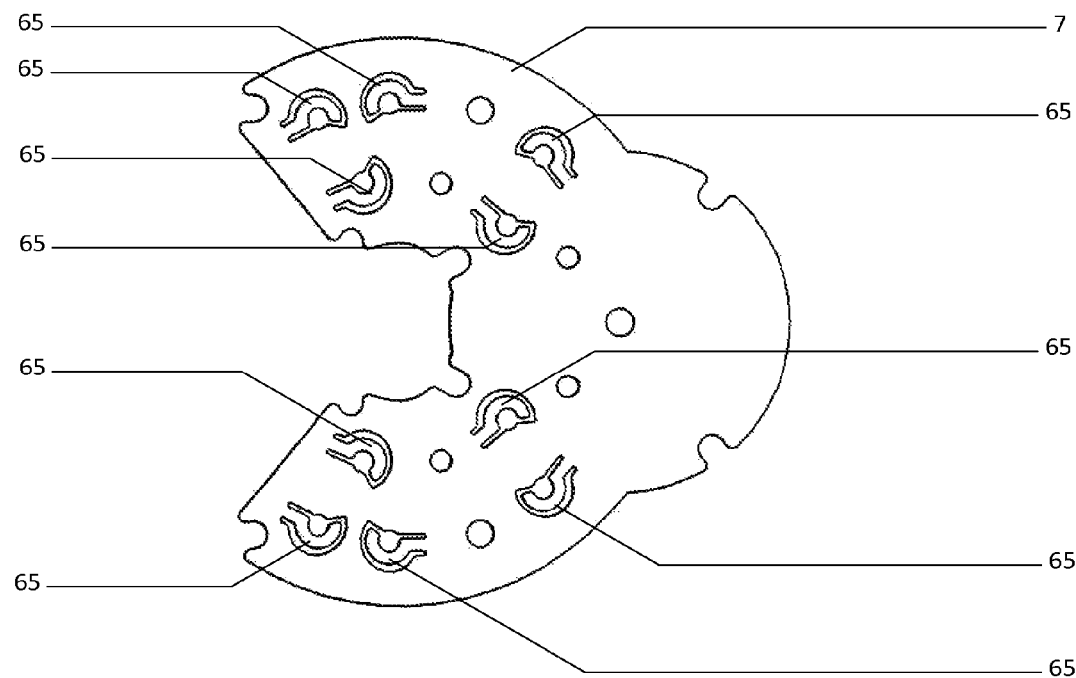
FIG. 20 shows a top view of the spring plate of the suturing device of FIG. 1.
Figure 21:
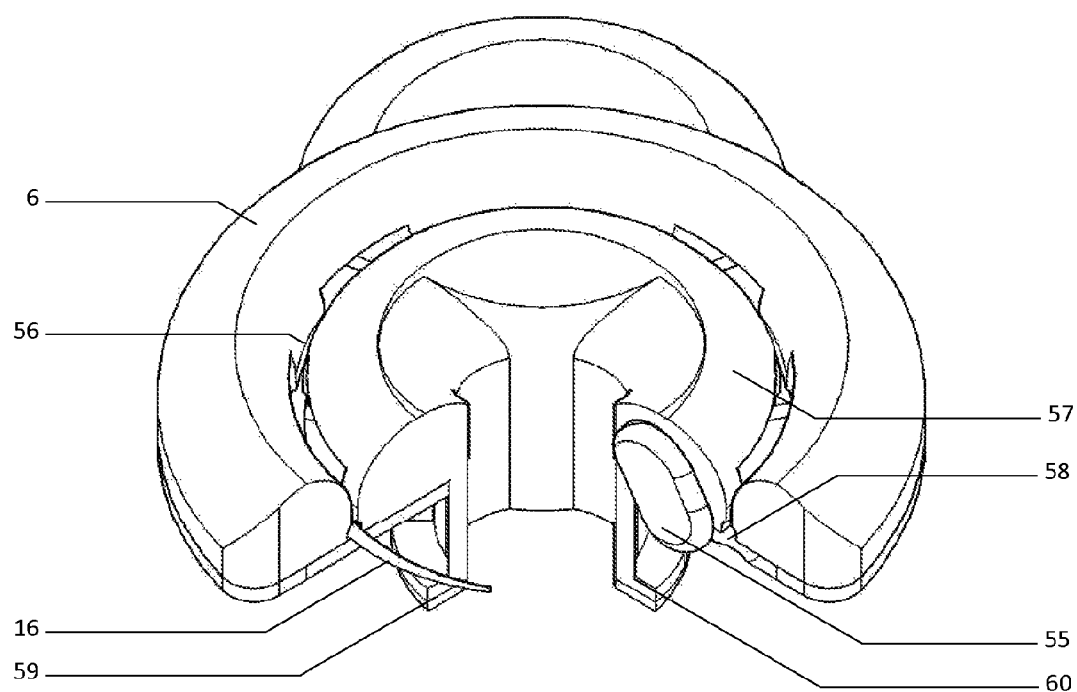
FIG. 21 shows an isometric view of the needle cartridge of the suturing head of the suturing device of FIG. 1.
Figure 22:
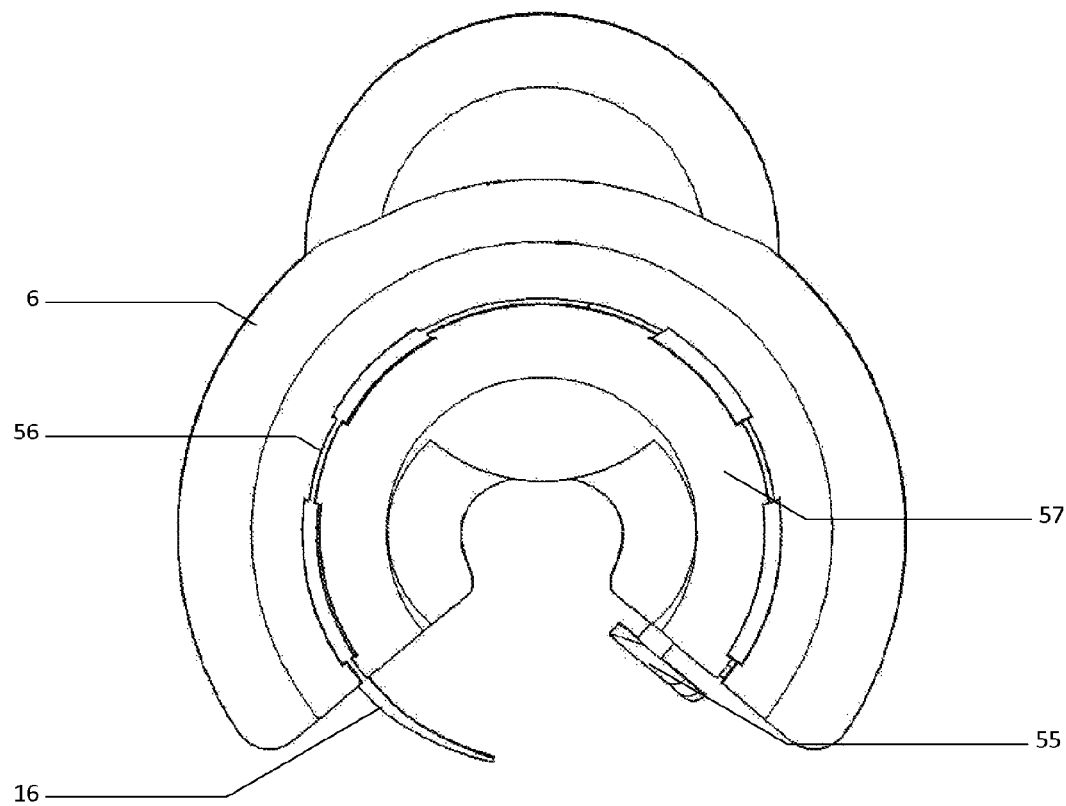
FIG. 22 shows a top view of the needle cartridge of the suturing head of the suturing device of FIG. 1.
Figure 23:
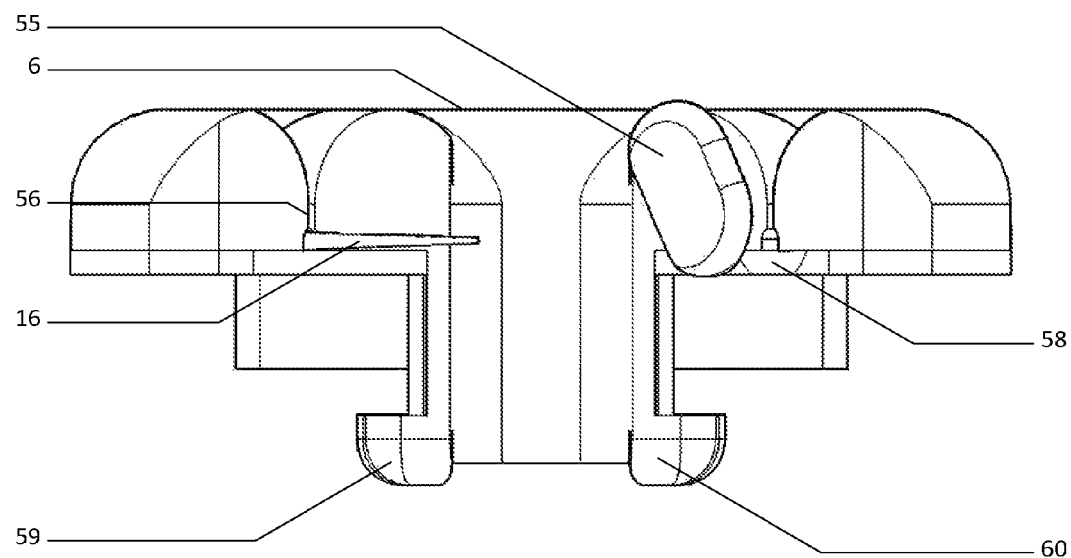
FIG. 23 shows a side view of the needle cartridge of the suturing head of the suturing device of FIG. 1.
Figure 24:
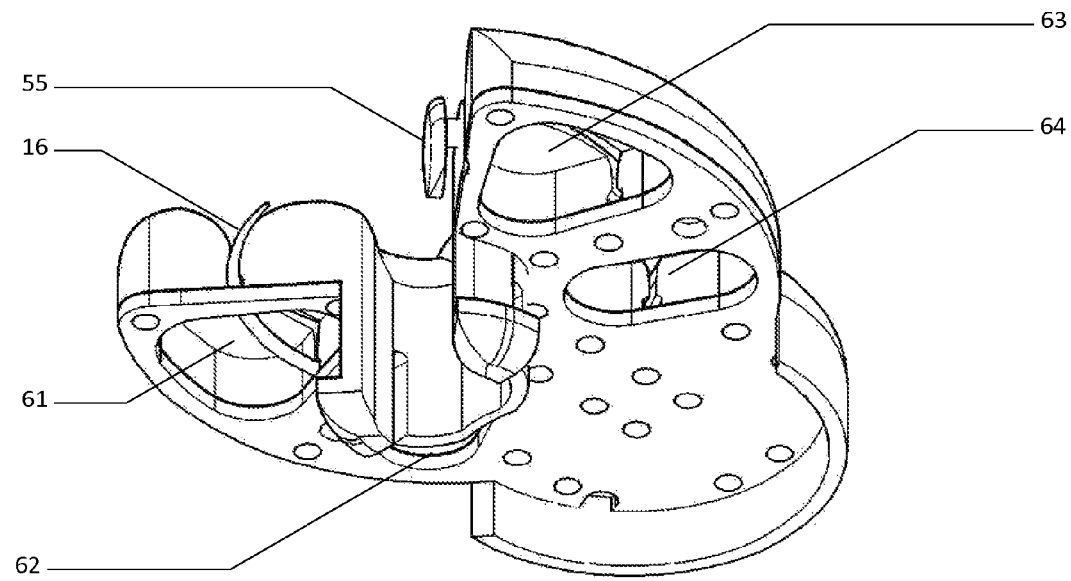
FIG. 24 shows an isometric view of the bottom of the needle cartridge of the suturing head of the suturing device of FIG. 1.
Figure 57:
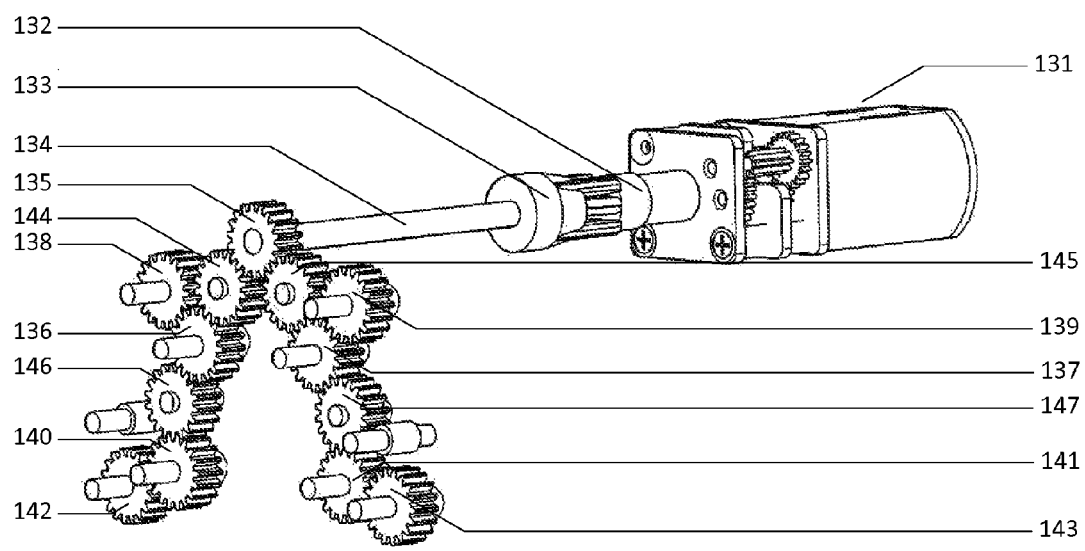
FIG. 57 shows an isometric view of the drive train of the suturing device of FIG. 34.
Figure 58:
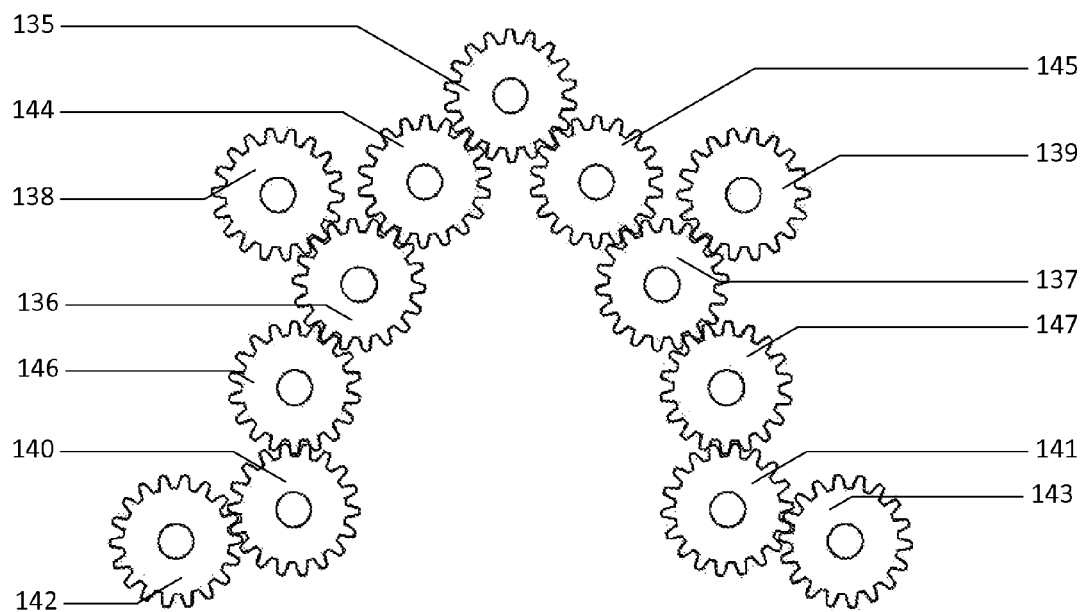
FIG. 58 shows a top view of the series of cogs of the suturing device of FIG. 34.
Figure 59:
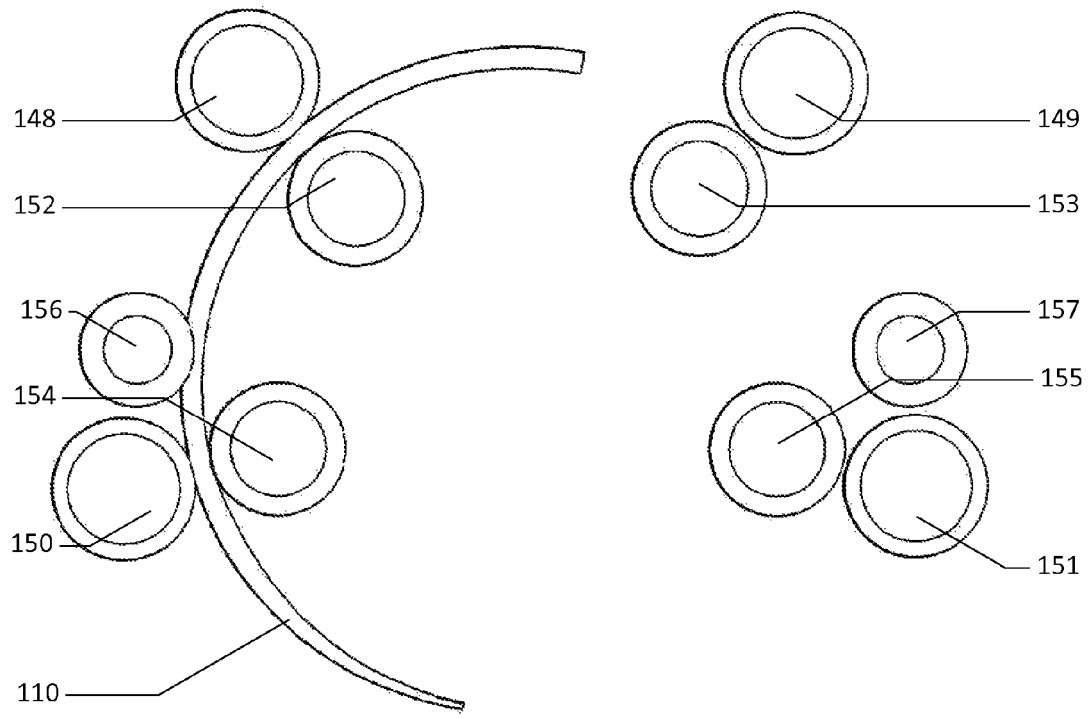
FIG. 59 shows a top view of the series of rollers of the suturing device of FIG. 34.
Figure 60:
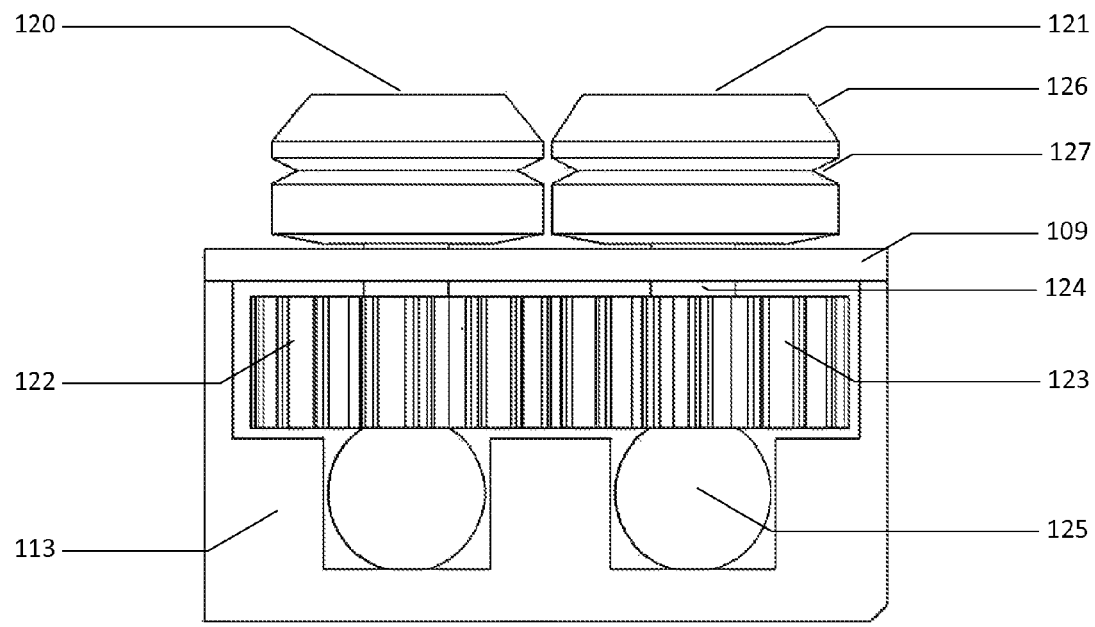
FIG. 60 shows a cross section side view of the head section of the suturing device of FIG. 34 with an inner and outer drive roller, corresponding drive cogs and cog shafts with spherical bases in the starting position.
Figure 61:
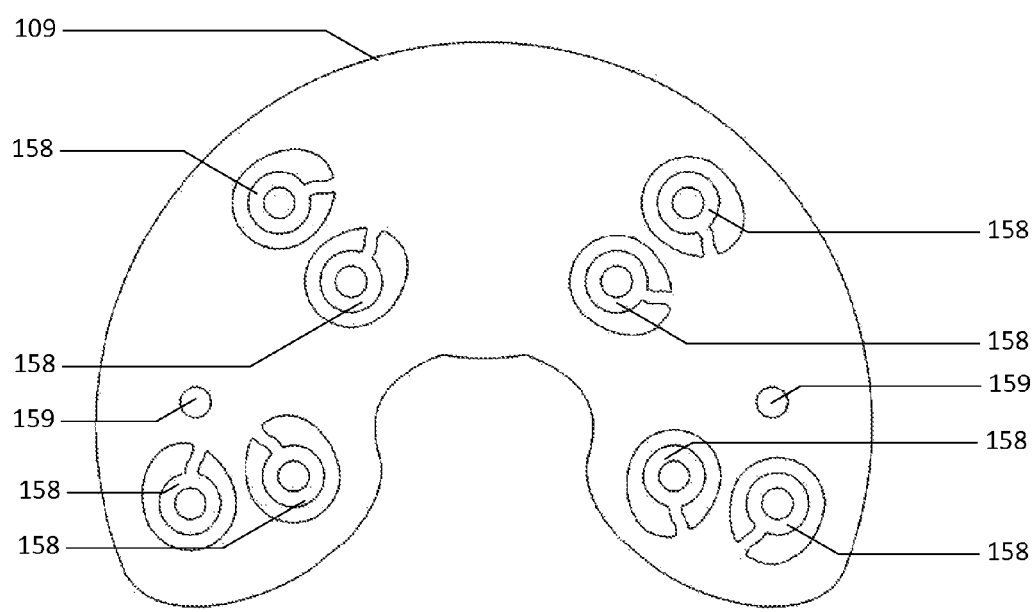
FIG. 61 shows a top view of the spring plate within the head section of the suturing device of FIG. 34 with the spring elements in the starting position.

FIGS. 57 to 59 show the arrangement of the shafts and cogs of the suturing head 103. The main drive cog 135 engages with intermediate drive cogs 144 and 145, each of which is mounted on a respective fixed shaft 130. Intermediate cogs 144 and 145 further engage with inner drive cogs 136 and 137, each of which is mounted on a respective cog shaft 124. Inner drive cogs 136 and 137 further engage with intermediate cogs 146 and 147, each of which is mounted on a respective fixed shaft 130. Inner drive cogs 136 and 137 further engage with outer drive cogs 138 and 139, each of which is mounted on a respective cog shaft 124. Intermediate cogs 146 and 147 further engage with inner drive cogs 140 and 141, each of which is mounted on a respective cog shaft 124. Inner drive cogs 140 and 141 further engage with outer drive cogs 142 and 143, each of which is respectively mounted on a cog shaft 124 with a spherical base 125 as shown in FIGS. 19 and 20.

Figure 52:
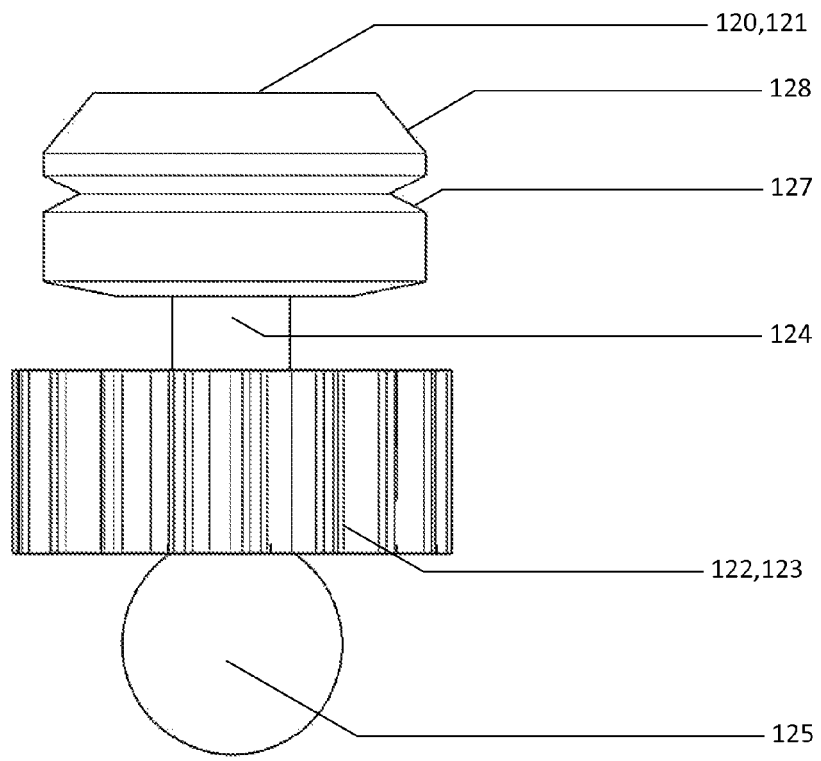
FIG. 52 shows a side view of the drive roller and corresponding cog and shaft with spherical base of the suturing head of the suturing device of FIG. 34.
Figure 53:
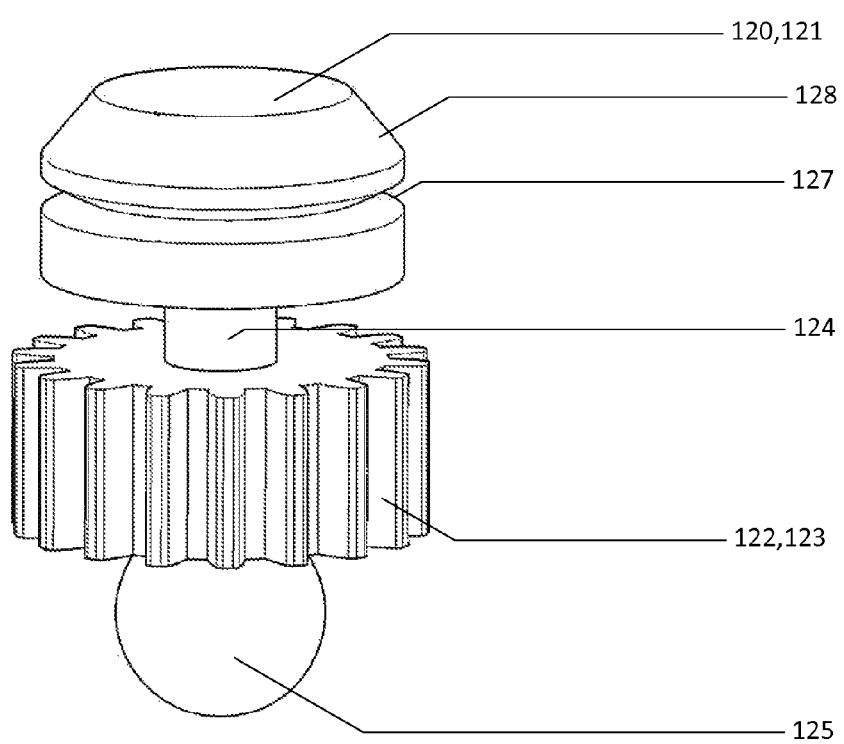
FIG. 53 shows an isometric view of the drive roller and corresponding cog and shaft with spherical base of the suturing head of the suturing device of FIG. 34.
Figure 54:
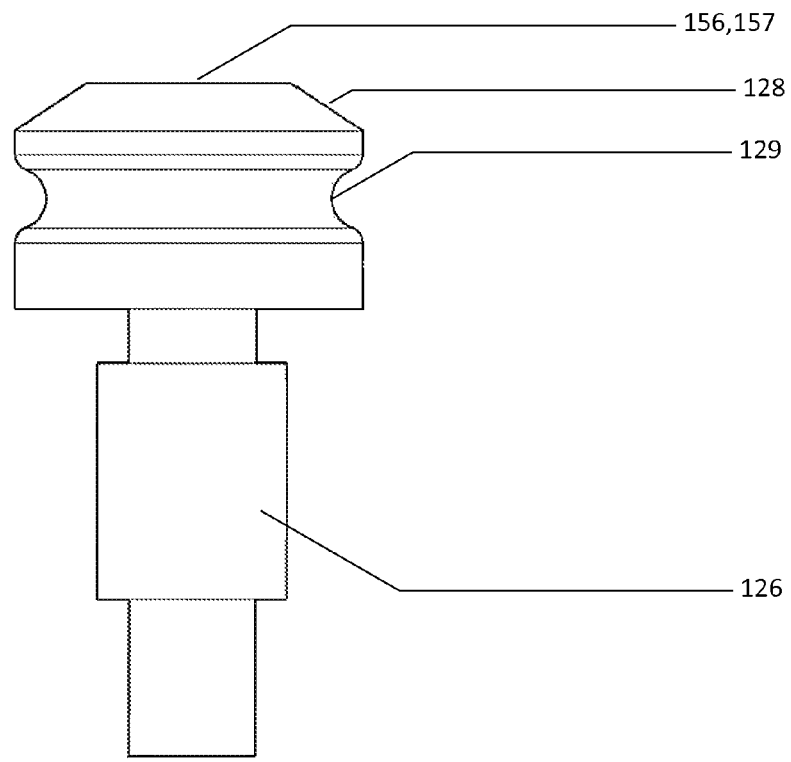
FIG. 54 shows a side view of the stabiliser roller and corresponding shaft of the suturing head of the suturing device of FIG. 34.
Figure 55:
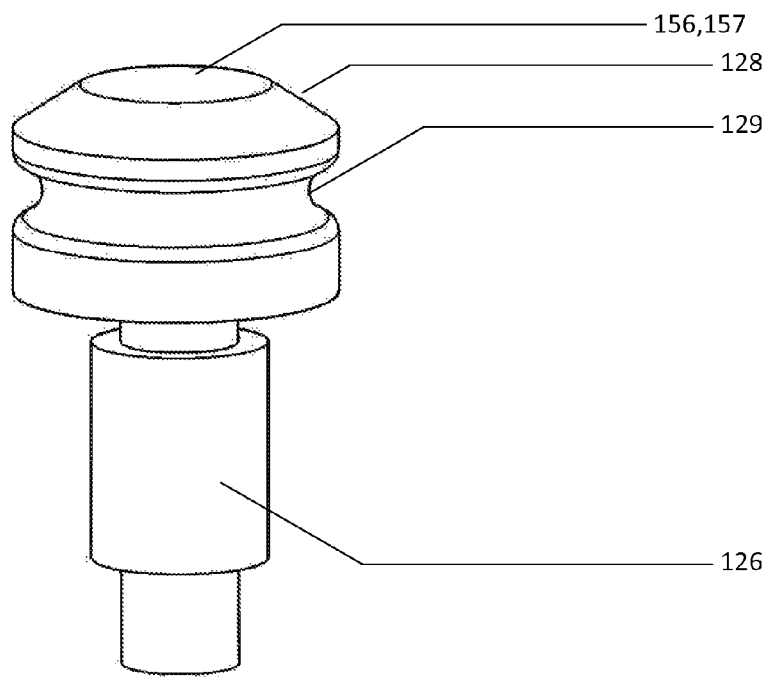
FIG. 55 shows an isometric view of the stabiliser roller and corresponding shaft of the suturing head of the suturing device of FIG. 34.
Figure 56:
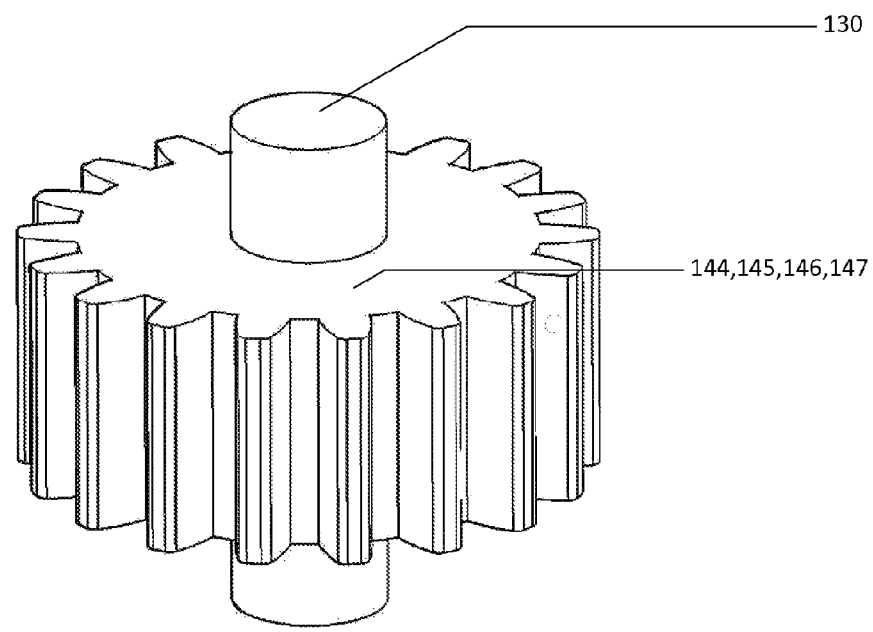
FIG. 56 shows an isometric view of the straight shafted intermediate cog of the suturing device of FIG. 34.

The cog shafts 124 upon which inner drive cogs 136, 137, 140 and 141 and outer drive cogs 138, 139, 142 and 143 are mounted are shown in detail in FIGS. 52 and 53. As can be seen, the cog shafts 124 have a spherical base 125. The cog shafts also have mounted on them inner or outer drive rollers, which can be seen in FIGS. 52 and 53, but for clarity are not shown in FIG. 57. The inner drive rollers 152, 153, 154 and 155 and outer drive rollers 148, 149, 150 and 151 are of a same design V-groove 127 sized proportionally to correspond with the difference in diameter between the inner and outer diameter of the needle.

The suturing head 103 further comprises stabilising rollers 156 and 157 each mounted on a respective shouldered shaft 126. The shouldered shafts 126 are shown in detail in FIGS. 54 and 55. The arrangement of the shouldered shafts 126, which are positioned near the outer drive rollers 142 and 143, is shown in FIG. 57 (the stabilising rollers are not shown for clarity). The stabilising rollers 152 and 153 are of a circular groove design 129, and contact the outside of the needle so as to act to keep the needle in the circular path.

Figure 62:
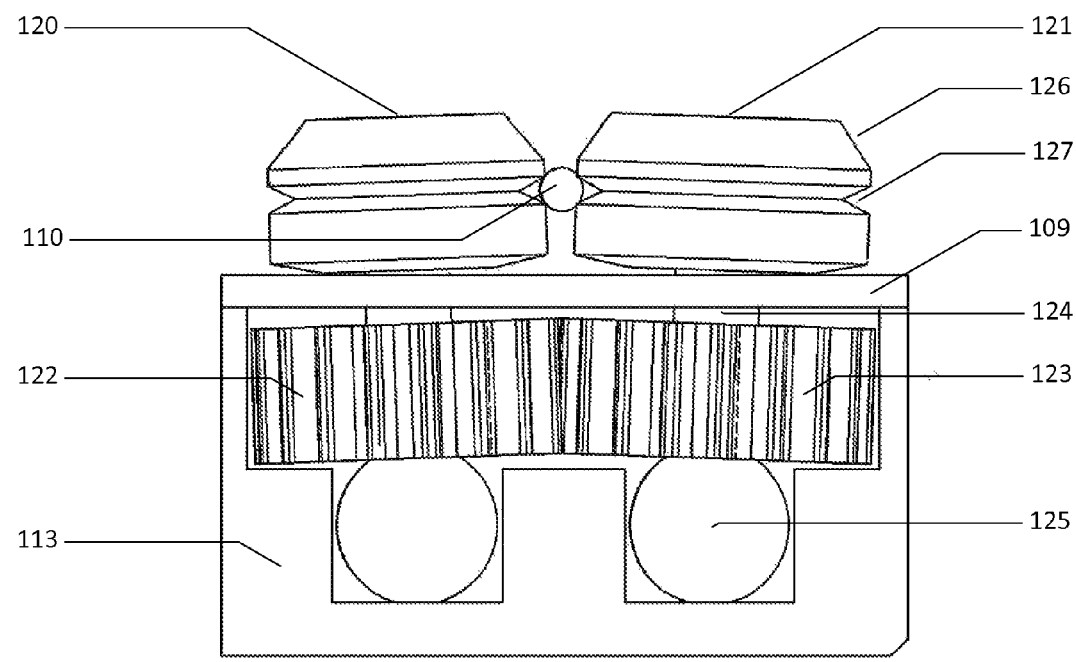
FIG. 62 shows a cross section side view of the head section of the suturing device of FIG. 34 with an inner and outer drive roller, corresponding drive cogs and cog shafts with spherical bases rotated due to the inclusion of the needle.
Figure 63:
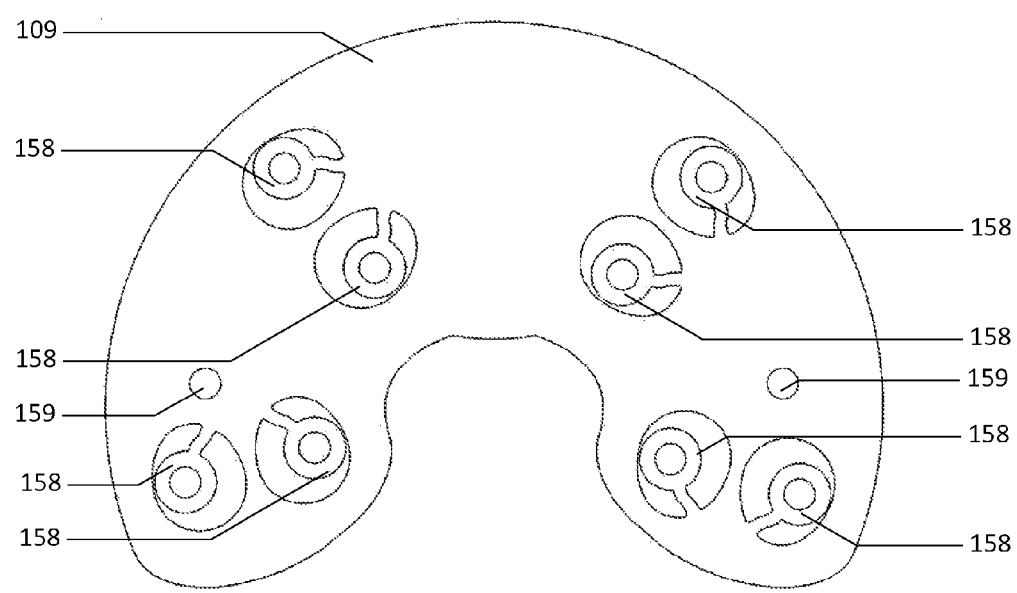
FIG. 63 shows a top view of the spring plate within the head section of the suturing device of FIG. 34 with the spring elements under tension rotated due to the inclusion of the needle.

As shown in particular in FIGS. 60 to 63, the suturing head 103 comprises a spring plate 109. Alternative embodiments of the spring plate are shown in FIGS. 66 to 69. The spring plate 109 comprises a sheet of resilient material, for example suitable metal or plastic, in which a plurality of voids form drive shaft spring elements 158 and shouldered shaft alignment apertures 159. The spring plate 109 is positioned in the suturing head body 113 so that each cog shaft 124 with spherical base 125 passes through and is retained by a shaft spring element 158. The spherical base 125 of each cog shaft is seated in a shaft bore hole in the suturing head body 113, which allows the shaft to move from the vertical position. This action allows the oppositely placed inner drive roller 120 and outer drive roller 121, mounted on their corresponding cog shaft 124 with spherical base 125, to move perpendicularly to the needle 116 to allow for the passage of the tapered and non-tapered section of the needle between the oppositely placed inner drive roller 120 and outer drive roller 121, while the drive shaft spring element 158 provides mechanical tension that acts to increase the grip upon the needle by the oppositely placed inner drive and outer drive rollers. The movement from vertical of the inner drive roller 120 and corresponding inner drive cog 122 and outer drive roller 121 and corresponding outer drive cog 123 mounted on their respective cog shafts 124 through their respective drive shaft spring element 158 is limited by the travel distance of the drive shaft spring element 158 under tension as shown in FIGS. 62 and 63.

The inner drive rollers 152, 153, 154 and 155 are arranged so that the diametrically interior surface of the curved suturing needle 10, which lies in the open groove 115 of the needle cartridge 105, engages with the V-groove 127 at the centre of the drive roller. The outer drive rollers 148, 149, 150 and 151 are arranged so that the diametrically exterior surface of the curved suturing needle 110, which lies in the open groove 115 of the needle cartridge 105, engages with the V-groove 127 at the centre of the outer drive roller. In particular, outer drive roller 150 and stabilising roller 156 are arranged opposite inner drive roller 154 in a triangular arrangement. Similarly, outer drive roller 151 and stabilising roller 157 are arranged opposite inner drive roller 150 in a triangular arrangement. Outer drive roller 148 is arranged opposite inner drive roller 152, and outer drive roller 149 is arranged opposite inner drive roller 153.

In an alternative embodiment, the drive rollers have a groove containing teeth that grip the needle. In another alternative embodiment, the drive rollers are made of a porous material and have a coating of a rubber material to grip the needle.

Figure 36:
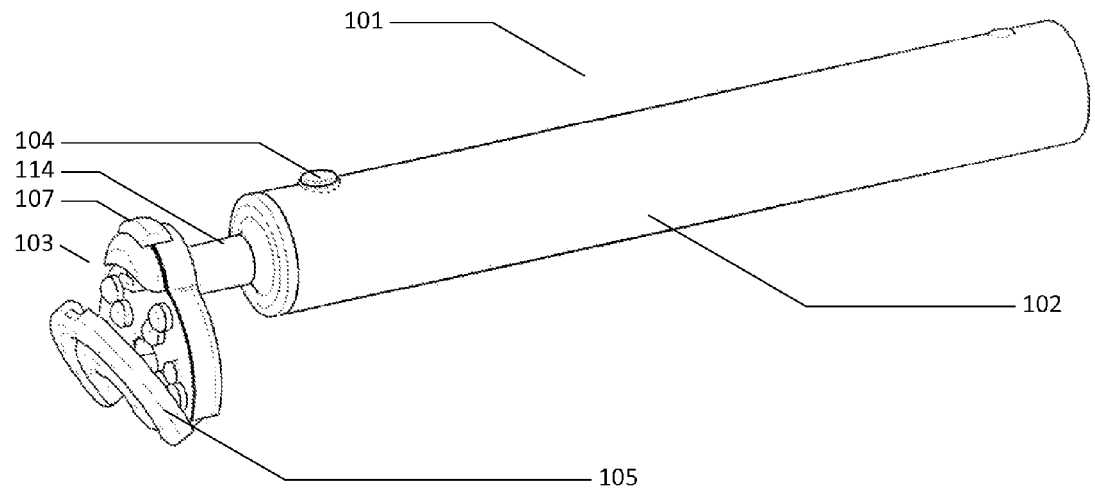
FIG. 36 shows an isometric view of the suturing device of FIG. 34 with the needle cartridge partly removed.

The needle cartridge 105 is shown in detail in FIGS. 46 to 51. The needle cartridge 105 holds a curved suturing needle 110 with a thread (not shown) extending from the non-tapered end of the needle in an open groove 115. The thread is guided out of the body of the cartridge during use by the filleted side of the open groove 116 on re-entry of the needle into the open groove 115 of needle cartridge 105, and also held out of the body of the cartridge by the chamfered filleted side of the open groove 116 of the open groove 115. The needle cartridge is attached to and removed from the suturing head 103 by depressing an eject button 107 and rotating the needle cartridge 105 about the retention tabs 117 until the needle has exited the V-grooves in the drive rollers, as shown in FIG. 36. The retention tabs may also be incorporated as part of the spring plate 109 (not shown). The open groove 115 in the needle cartridge 105 in cross-section consists of a major arc that retains the needle 110 within the body of the needle cartridge 105 while allowing the thread to stay extended to the exterior of the needle cartridge.

The indentations 119 on the underside of the needle cartridge 105 allow for the inner drive rollers 152, 153, 154 and 155, outer drive rollers 148, 149, 150 and 151, and stabilising rollers 156 and 157 to protrude into the needle cartridge 105 to allow them to drive to the needle 110.

In use, the device is controlled by a user by means of the control switch 104 which in turn through the integrated circuit board 163 operates the motor 131 with the drive coupling plug 132 attached, powered by the power cells 162. The drive coupling plug 132 engages with the drive coupling socket 133 which is attached to the drive shaft 134 which ends in the main drive cog 135, causing the main drive cog 135, and consequently the other cogs in the suturing head 103, to move. This results in the rotation of the inner drive rollers 152, 153, 154 and 155 and the outer drive rollers 148, 149, 150 and 151, which causes the suturing needle 110 to rotate around a circular path incorporating the open groove 115 of the needle cartridge 15 by means of the friction provided by the V-grooves 127 of the inner drive rollers and outer drive rollers and under tension provided by the drive shaft spring elements 158 of the spring plate 109, with additional rotational stability provided by stabilising rollers 156 and 157 held in alignment by the shouldered shaft alignment aperture 159 of the spring plate 109.

The suturing needle 110 is at all times held in alignment in the circular path regardless of its position in the circular path, as in all positions it will be held by the V-groove 127 drive surfaces of at least one outer drive roller and the circular groove 129 of at least one stabilising rollers in the correct position within the V-groove of the corresponding inner drive rollers.

The roller chamfered edges 128 of the inner drive rollers and outer drive rollers above the V-grooves 127 and the roller chamfered edges 128 of the stabilising rollers above the circular grooves 129 allow for the easy passage of the needle 110 into and out of the V-grooves 127 and circular grooves 129 of the drive and stabilising rollers during insertion or removal of the needle cartridge 105.

The triangular arrangement of the inner drive roller 154, the outer roller 150 and the stabilising roller 156 in particular act to hold the suturing needle 110 in alignment and act to prevent the suturing needle 110 rotating about its centre and so moving out of alignment with the circular path even when it is almost completely outside the semi-circular portion of the head body 113 and needle cartridge 105.

Should the suturing needle 110 nevertheless be moved out of alignment when any portion of it is outside the semi-circular portion of the head body 113 and needle cartridge 105, for example because the suturing needle is passing through particularly dense or hardened tissue, when re-entering the head body 113 and needle cartridge 105, the tip of the suturing needle 110 will be guided by the cone-shaped indentation 118 at the first end of the needle cartridge 105 back into the correct alignment.

In use, the suturing needle 110 will of course be being used to suture using suturing thread. During suturing, the suture thread is able to pass through the open groove 115 to rotate outside of the constraints of the semi-circular portion of needle cartridge 105, thus allowing the device to be used for suturing without the device being attached to the tissue being sutured.

The control assembly may be controlled by the user by means of the control switch 104 and power button 160 as follows. The user presses the control switch 104 down towards the handle 102 (i.e. "clicks" it) to rotate anti-clockwise and partly exit the needle 110 from the open groove 115 of the needle cartridge 105. The user then inserts the partly exposed needle into the first section of tissue to be sutured. The use then presses the control switch 104 again which causes the suturing needle 110 to rotate anti-clockwise in one complete rotation around the circular path so that the needle 110 returns and sits entirely within the body of the needle cartridge 105, thus completing one suture. Further, as upon completion of the suture the needle 110 is entirely within the body of the needle cartridge 105, the needle cartridge 106 can be removed from the suturing head 103 and replaced and disposed of safely.

However, while a particularly convenient system for operating the suturing device has been described, the skilled person will appreciate that any other suitable system could be used.

Whilst the present invention has been described and illustrated with reference to particular embodiments, it will be appreciated by those of ordinary skill in the art that the invention lends itself to many different variations not specifically illustrated herein.

The invention claimed is:

1. A replaceable suturing head for a suturing device, the suturing head comprising:
   a suturing portion;
   wherein the suturing portion comprises a curved suturing needle arranged to move around a circular path defined by a plurality of rollers mounted on roller shafts within the suturing portion, at least one of the plurality of rollers being a drive roller driven by the drive motor to move the suturing needle around the circular path;
   wherein one or more of the roller shafts comprises a base, and the one or more roller shafts is mounted within the suturing portion so that the one or more roller shafts can pivot around the base; and
   wherein the suturing portion comprises biasing means for biasing the one or more roller shafts so that the one or more rollers is biased towards the suturing needle.

2. A suturing head as claimed in claim 1, wherein the base of the one or more roller shafts has a spherically-shaped end.

3. A suturing head as claimed in claim 1, wherein the biasing means is a spring plate mounted in parallel with the circular path of the suturing needle.

4. A suturing head as claimed in claim 3, wherein the spring plate comprises a plurality of voids, and wherein the roller shafts extend through the holes formed by the voids.

5. A suturing head as claimed in claim 4, wherein the voids in the spring plate form shaft springs in the spring plate that press against the roller shafts.

6. A suturing head as claimed in claim 1, wherein the suturing portion of the replaceable suturing head comprises a body portion, and a replaceable needle cartridge containing the suturing needle.

7. A suturing head as claimed in claim 6, wherein the plurality of rollers are mounted on the body portion, and the replaceable needle cartridge comprises indentations into which the rollers extend to allow the rollers to contact the suturing needle.

8. A suturing head as claimed in claim 1, wherein a rotational surface of at least one of the plurality of rollers is arranged to provide an indented drive surface.

9. A suturing head as claimed in claim 1, wherein at least one of the plurality of rollers comprises a rotational surface, and a plurality of slotted recesses extending inwardly from the rotational surface.

10. A suturing head as claimed in claim 1, wherein the plurality of rollers comprise a first roller arranged on a first side of the circular path, and corresponding second roller and third rollers arranged on the opposite side of the circular path from the first drive roller, and wherein the first, second and third rollers act to hold the suturing needle in the circular path.

11. A suturing head as claimed in claim 1, wherein the body portion of the suturing portion comprises a cone-shaped indentation located on the circular path to guide an incoming the end of the suturing needle into alignment with the circular path.

12. A suturing head as claimed in claim 1, comprising a light to illuminate the suturing needle when the suturing needle exits the body portion.

13. A suturing head as claimed in claim 1, wherein the body portion of the suturing portion is open on a first side of the circular path.

14. A suturing head as claimed in claim 1, further comprising: a replaceable needle cartridge for the replaceable suturing head.

15. A suturing device, comprising:
    a control assembly comprising a drive motor and a control apparatus for controlling the drive motor; and
    a replaceable suturing head for the suturing device, the suturing head comprising a suturing portion;
    wherein the suturing portion comprises a curved suturing needle arranged to move around a circular path defined by a plurality of rollers mounted on roller shafts within the suturing portion, at least one of the plurality of rollers being a drive roller driven by the drive motor to move the suturing needle around the circular path;
    wherein one or more of the roller shafts comprises a base, and the one or more roller shafts is mounted within the suturing portion so that the one or more roller shafts can pivot around the base; and
    wherein the suturing portion comprises a biasing structure configured to bias the one or more roller shafts so that the one or more rollers is biased towards the suturing needle.

16. A suturing device as claimed in claim 15, wherein the control assembly is arranged, in response to an input from a user, to position the suturing needle fully within the body portion of the suturing portion for removal of the replaceable cartridge within the replaceable suturing head.

17. A suturing device as claimed in claim 15, wherein the control assembly is arranged, in response to an input from a user, to rotate the suturing needle once around the circular path.

18. A suturing device as claimed in claim 16, wherein the control assembly is arranged, in response to an input from a user, to rotate the suturing needle once around the circular path.

\* \* \* \* \*